US009289289B2

(12) United States Patent
Rolando et al.

(10) Patent No.: US 9,289,289 B2
(45) Date of Patent: Mar. 22, 2016

(54) SUTURELESS ANCHORING DEVICE FOR CARDIAC VALVE PROSTHESES

(75) Inventors: Giovanni Rolando, Chivasso (IT); Mauro Ercolani, Rome (IT); Paolo Gaschino, Castagneto Po (IT); Andrea Marchisio, Ivrea (IT)

(73) Assignee: Sorin Group Italia S.r.l., Milan (IT)

( * ) Notice: Subject to any disclaimer, the term of this patent is extended or adjusted under 35 U.S.C. 154(b) by 89 days.

(21) Appl. No.: 13/985,100

(22) PCT Filed: Feb. 10, 2012

(86) PCT No.: PCT/IB2012/050608
§ 371 (c)(1),
(2), (4) Date: Nov. 1, 2013

(87) PCT Pub. No.: WO2012/110929
PCT Pub. Date: Aug. 23, 2012

(65) Prior Publication Data
US 2014/0052243 A1 Feb. 20, 2014

(30) Foreign Application Priority Data

Feb. 14, 2011 (EP) .................................... 11425030

(51) Int. Cl.
*A61F 2/24* (2006.01)
(52) U.S. Cl.
CPC ............. *A61F 2/2409* (2013.01); *A61F 2/2403* (2013.01); *A61F 2250/006* (2013.01)
(58) Field of Classification Search
CPC ... A61F 2/2409; A61F 2/2424; A61F 2/2445; A61F 2002/0823; A61F 2002/0829; A61F 2002/0864; A61F 2002/087

USPC ......................................................... 623/2.16
See application file for complete search history.

(56) References Cited

U.S. PATENT DOCUMENTS 3,143,742 A * 8/1964 Cromie ........................ 623/2.38
3,334,629 A 8/1967 Cohn
3,363,442 A 1/1968 Kennedy et al.
(Continued)

FOREIGN PATENT DOCUMENTS

CN 101011298 A 8/2007
DE 3640745 A1 6/1987
(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Yashita Sharma
*Assistant Examiner* — Wade P Schutte
(74) *Attorney, Agent, or Firm* — Faegre Baker Daniels LLP

(57) ABSTRACT

A device for anchoring a prosthetic heart valve on biological tissue, includes first and second anchoring assemblies, mutually couplable to secure biological tissue therebetween. The anchoring assemblies include at least one pair of complementary arched portions having anchoring formations for anchoring on the biological tissue. The anchoring formations include integral extensions of the anchoring assemblies extending radially outwardly of one of the anchoring assemblies.

16 Claims, 15 Drawing Sheets

(56) References Cited

U.S. PATENT DOCUMENTS

| | | |
|---|---|---|
| 3,409,013 A | 11/1968 | Berry |
| 3,540,431 A | 11/1970 | Mobin-Uddin |
| 3,546,710 A | 12/1970 | Shumakov et al. |
| 3,574,865 A | 4/1971 | Hamaker |
| 3,587,115 A | 6/1971 | Shiley |
| 3,608,097 A | 9/1971 | Bellhouse et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,744,060 A | 7/1973 | Bellhouse et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,086,665 A | 5/1978 | Poirier |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,451,936 A | 6/1984 | Carpentier et al. |
| 4,470,157 A | 9/1984 | Love |
| 4,477,930 A | 10/1984 | Totten et al. |
| 4,501,030 A | 2/1985 | Lane |
| 4,506,394 A | 3/1985 | Bedard |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,624,822 A | 11/1986 | Arru et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,692,164 A | 9/1987 | Dzemeshkevich et al. |
| 4,710,192 A | 12/1987 | Liotta et al. |
| 4,733,665 A | 3/1988 | Palmaz |
| 4,758,151 A | 7/1988 | Arru et al. |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goerne et al. |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,042,161 A | 8/1991 | Hodge |
| 5,047,041 A | 9/1991 | Samuels |
| 5,059,177 A | 10/1991 | Towne et al. |
| 5,061,273 A | 10/1991 | Yock |
| 5,084,151 A | 1/1992 | Vallana et al. |
| 5,085,635 A | 2/1992 | Cragg |
| 5,089,015 A | 2/1992 | Ross |
| 5,123,919 A | 6/1992 | Sauter et al. |
| 5,133,845 A | 7/1992 | Vallana et al. |
| 5,139,515 A | 8/1992 | Robicsek |
| 5,152,771 A | 10/1992 | Sabbaghian et al. |
| 5,161,547 A | 11/1992 | Tower |
| 5,163,953 A | 11/1992 | Vince |
| 5,163,954 A | 11/1992 | Curcio et al. |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,300,086 A | 4/1994 | Gory et al. |
| 5,314,468 A | 5/1994 | Ramos Martinez |
| 5,327,774 A | 7/1994 | Nguyen et al. |
| 5,332,402 A | 7/1994 | Teitelbaum |
| 5,350,398 A | 9/1994 | Pavcnik et al. |
| 5,360,014 A | 11/1994 | Sauter et al. |
| 5,370,684 A | 12/1994 | Vallana et al. |
| 5,370,685 A | 12/1994 | Stevens |
| 5,387,247 A | 2/1995 | Vallana et al. |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,423,886 A | 6/1995 | Arru et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,296 A | 2/1996 | Love et al. |
| 5,489,297 A | 2/1996 | Duran |
| 5,496,346 A | 3/1996 | Horzewski et al. |
| 5,507,767 A | 4/1996 | Maeda et al. |
| 5,522,884 A | 6/1996 | Wright |
| 5,545,209 A | 8/1996 | Roberts et al. |
| 5,545,211 A | 8/1996 | An et al. |
| 5,545,214 A | 8/1996 | Stevens |
| 5,545,215 A | 8/1996 | Duran |
| 5,554,185 A | 9/1996 | Block et al. |
| 5,560,487 A | 10/1996 | Starr |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,669,919 A | 9/1997 | Sanders et al. |
| 5,672,169 A | 9/1997 | Verbeek |
| 5,674,277 A | 10/1997 | Freitag |
| 5,693,066 A | 12/1997 | Rupp et al. |
| 5,695,498 A | 12/1997 | Tower |
| 5,698,307 A | 12/1997 | Levy |
| 5,702,368 A | 12/1997 | Stevens et al. |
| 5,712,953 A | 1/1998 | Langs |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,776,187 A | 7/1998 | Krueger et al. |
| 5,782,809 A | 7/1998 | Umeno et al. |
| 5,800,456 A | 9/1998 | Maeda et al. |
| 5,800,508 A | 9/1998 | Goicoechea et al. |
| 5,800,531 A | 9/1998 | Cosgrove et al. |
| 5,807,405 A | 9/1998 | Vanney et al. |
| 5,810,873 A | 9/1998 | Morales |
| 5,814,096 A | 9/1998 | Lam et al. |
| 5,817,126 A | 10/1998 | Imran |

(56) References Cited

U.S. PATENT DOCUMENTS

| | | |
|---|---|---|
| 5,824,037 A | 10/1998 | Fogarty et al. |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,843,244 A | 12/1998 | Pelton et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Twoer |
| 5,860,996 A | 1/1999 | Urban et al. |
| 5,861,028 A | 1/1999 | Angell |
| 5,868,783 A | 2/1999 | Tower |
| 5,876,436 A | 3/1999 | Vanney et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,891,195 A | 4/1999 | Klostermeyer et al. |
| 5,906,619 A | 5/1999 | Olson et al. |
| 5,907,893 A | 6/1999 | Zadno Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,947,993 A | 9/1999 | Morales |
| 5,951,540 A | 9/1999 | Verbeek |
| 5,954,766 A | 9/1999 | Zadno Azizi et al. |
| 5,957,949 A | 9/1999 | Leonhardt et al. |
| 5,968,068 A | 10/1999 | Dehdashtian et al. |
| 5,972,016 A | 10/1999 | Morales |
| 5,980,570 A | 11/1999 | Simpson |
| 5,984,957 A | 11/1999 | Laptewicz, Jr. et al. |
| 5,997,573 A | 12/1999 | Quijano et al. |
| 6,010,531 A | 1/2000 | Donlon et al. |
| 6,019,739 A | 2/2000 | Rhee et al. |
| 6,019,790 A | 2/2000 | Holmberg et al. |
| 6,022,370 A | 2/2000 | Tower |
| 6,024,737 A | 2/2000 | Morales |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV et al. |
| 6,051,002 A | 4/2000 | Morales |
| 6,051,014 A | 4/2000 | Jang |
| 6,051,104 A | 4/2000 | Oriaran et al. |
| 6,059,809 A | 5/2000 | Amor et al. |
| 6,059,827 A | 5/2000 | Fenton, Jr. |
| 6,063,102 A | 5/2000 | Morales |
| 6,110,200 A | 8/2000 | Hinnenkamp |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,187,016 B1 | 2/2001 | Hedges et al. |
| 6,197,143 B1 | 3/2001 | Bodnar |
| 6,200,336 B1 | 3/2001 | Pavcnik et al. |
| 6,202,272 B1 | 3/2001 | Jackson |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillon et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,270,526 B1 | 8/2001 | Cox |
| 6,277,110 B1 | 8/2001 | Morales |
| 6,277,555 B1 | 8/2001 | Duran et al. |
| 6,287,339 B1 | 9/2001 | Vazquez et al. |
| 6,299,637 B1 | 10/2001 | Shaolian et al. |
| 6,299,638 B1 | 10/2001 | Sauter |
| 6,302,906 B1 | 10/2001 | Goicoechea et al. |
| 6,309,382 B1 | 10/2001 | Garrison et al. |
| 6,309,383 B1 | 10/2001 | Campbell et al. |
| 6,309,417 B1 | 10/2001 | Spence et al. |
| 6,312,462 B1 | 11/2001 | McDermott et al. |
| 6,338,735 B1 | 1/2002 | Stevens |
| 6,348,063 B1 | 2/2002 | Yassour et al. |
| 6,350,277 B1 | 2/2002 | Kocur |
| 6,350,281 B1 | 2/2002 | Rhee |
| 6,352,547 B1 | 3/2002 | Brown et al. |
| 6,352,554 B2 | 3/2002 | De Paulis |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,387,117 B1 | 5/2002 | Arnold, Jr. et al. |
| 6,398,807 B1 | 6/2002 | Chouinard et al. |
| 6,402,780 B2 | 6/2002 | Williamson, IV et al. |
| 6,409,750 B1 | 6/2002 | Hyodoh et al. |
| 6,424,885 B1 | 7/2002 | Niemeyer et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,481,262 B2 | 11/2002 | Ching et al. |
| 6,482,228 B1 | 11/2002 | Norred |
| 6,488,704 B1 | 12/2002 | Connelly et al. |
| 6,493,608 B1 | 12/2002 | Niemeyer |
| 6,494,909 B2 | 12/2002 | Greenhalgh |
| 6,503,272 B2 | 1/2003 | Duerig et al. |
| 6,506,201 B2 | 1/2003 | Di Caprio et al. |
| 6,508,833 B2 | 1/2003 | Pavcnik et al. |
| 6,510,722 B1 | 1/2003 | Ching et al. |
| 6,527,800 B1 | 3/2003 | McGuckin, Jr. et al. |
| 6,530,949 B2 | 3/2003 | Konya et al. |
| 6,544,285 B1 | 4/2003 | Thubrikar et al. |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,598,307 B2 | 7/2003 | Love et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,629,350 B2 | 10/2003 | Motsenbocker |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,656,219 B1 | 12/2003 | Wiktor |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,684 B1 | 1/2004 | Morley et al. |
| 6,676,692 B2 | 1/2004 | Rabkin et al. |
| 6,676,698 B2 | 1/2004 | McGuckin, Jr. et al. |
| 6,678,962 B1 | 1/2004 | Love et al. |
| 6,679,893 B1 | 1/2004 | Tran |
| 6,682,558 B2 | 1/2004 | Tu et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |

(56) References Cited

U.S. PATENT DOCUMENTS

| | | |
|---|---|---|
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,726,713 B2 | 4/2004 | Schaldach, Jr. et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,161 B2 | 8/2004 | Brown et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence et al. |
| 6,805,711 B2 | 10/2004 | Quijano et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof et al. |
| 6,846,324 B2 | 1/2005 | Stobie |
| 6,846,325 B2 | 1/2005 | Liddicoat |
| 6,866,650 B2 | 3/2005 | Stevens et al. |
| 6,872,223 B2 | 3/2005 | Roberts et al. |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,915,560 B2 | 7/2005 | Austin |
| 6,929,653 B2 | 8/2005 | Strecter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,966,924 B2 | 11/2005 | Holmberg |
| 6,968,607 B2 | 11/2005 | Motsenbocker |
| 6,974,474 B2 | 12/2005 | Pavcnik et al. |
| 6,974,476 B2 | 12/2005 | McGuckin, Jr. et al. |
| 6,981,982 B2 | 1/2006 | Armstrong et al. |
| 6,986,742 B2 | 1/2006 | Hart et al. |
| 6,988,881 B2 | 1/2006 | Motsenbocker et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,007,396 B2 | 3/2006 | Rudko et al. |
| 7,018,401 B1 | 3/2006 | Hyodoh et al. |
| 7,018,404 B2 | 3/2006 | Holmberg et al. |
| 7,018,406 B2 | 3/2006 | Seguin et al. |
| 7,021,114 B2 | 4/2006 | Perreault |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,069,794 B2 | 7/2006 | Motsenbocker et al. |
| 7,097,659 B2 | 8/2006 | Woolfson et al. |
| 7,105,016 B2 | 9/2006 | Shiu et al. |
| 7,115,141 B2 | 10/2006 | Menz et al. |
| 7,125,418 B2 | 10/2006 | Duran et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,211,107 B2 | 5/2007 | Bruckheimer |
| 7,252,682 B2 | 8/2007 | Seguin |
| 7,255,706 B2 | 8/2007 | Rosengart |
| 7,258,698 B2 | 8/2007 | Lemmon |
| 7,261,732 B2 | 8/2007 | Justino |
| 7,276,078 B2 | 10/2007 | Spenser et al. |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin et al. |
| 7,329,279 B2 | 2/2008 | Haug et al. |
| 7,335,218 B2 | 2/2008 | Wilson et al. |
| 7,338,484 B2 | 3/2008 | Schoon et al. |
| 7,338,520 B2 | 3/2008 | Bailey et al. |
| 7,347,869 B2 | 3/2008 | Hojeibane et al. |
| 7,351,256 B2 | 4/2008 | Hojeibane et al. |
| 7,357,814 B2 | 4/2008 | Gabbay |
| 7,367,984 B2 | 5/2008 | Kulcinski et al. |
| 7,374,571 B2 | 5/2008 | Pease et al. |
| 7,377,938 B2 | 5/2008 | Sarac et al. |
| 7,377,941 B2 | 5/2008 | Rhee et al. |
| 7,381,218 B2 | 6/2008 | Schreck |
| 7,384,411 B1 | 6/2008 | Condado |
| 7,393,360 B2 | 7/2008 | Spenser et al. |
| 7,427,291 B2 | 9/2008 | Liddicoat et al. |
| 7,429,269 B2 | 9/2008 | Schwammenthal et al. |
| 7,442,204 B2 | 10/2008 | Schwammenthal et al. |
| 7,453,227 B2 | 11/2008 | Prisco et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,534,259 B2 | 5/2009 | Lashinski et al. |
| 7,544,206 B2 | 6/2009 | Cohn |
| 7,547,322 B2 | 6/2009 | Sarac et al. |
| 7,556,645 B2 | 7/2009 | Lashinski et al. |
| 7,556,646 B2 | 7/2009 | Yang et al. |
| 7,569,071 B2 | 8/2009 | Haverkost et al. |
| 7,578,843 B2 | 8/2009 | Shu |
| 7,585,321 B2 | 9/2009 | Cribier |
| 7,591,848 B2 | 9/2009 | Allen |
| 7,618,446 B2 | 11/2009 | Andersen et al. |
| 7,618,447 B2 | 11/2009 | Case et al. |
| 7,682,390 B2 | 3/2010 | Seguin |
| 7,708,775 B2 | 5/2010 | Rowe et al. |
| 7,780,726 B2 | 8/2010 | Seguin |
| 7,806,919 B2 | 10/2010 | Bloom et al. |
| 7,857,845 B2 | 12/2010 | Stacchino et al. |
| 7,972,378 B2 | 7/2011 | Tabor et al. |
| 7,981,153 B2 | 7/2011 | Fogarty et al. |
| 8,043,360 B2 * | 10/2011 | McNamara et al. ......... 623/1.15 |
| 8,083,793 B2 | 12/2011 | Lane et al. |
| 8,109,996 B2 | 2/2012 | Stacchino et al. |
| 8,535,373 B2 | 9/2013 | Stacchino et al. |
| 8,539,662 B2 | 9/2013 | Stacchino et al. |
| 8,540,768 B2 | 9/2013 | Stacchino et al. |
| 8,834,563 B2 | 9/2014 | Righini |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2001/0049558 A1 | 12/2001 | Liddicoat et al. |
| 2002/0010508 A1 | 1/2002 | Chobotov |
| 2002/0029014 A1 | 3/2002 | Jayaraman |
| 2002/0029783 A1 | 3/2002 | Stevens et al. |
| 2002/0032480 A1 | 3/2002 | Spence et al. |
| 2002/0032481 A1 | 3/2002 | Gabbay |
| 2002/0035390 A1 | 3/2002 | Schaldach et al. |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0058994 A1 | 5/2002 | Hill et al. |
| 2002/0058995 A1 | 5/2002 | Stevens |
| 2002/0072789 A1 | 6/2002 | Hackett et al. |
| 2002/0095209 A1 | 7/2002 | Zadno Azizi et al. |
| 2002/0103533 A1 | 8/2002 | Langberg et al. |

(56) References Cited

U.S. PATENT DOCUMENTS

| | | |
|---|---|---|
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0128702 A1 | 9/2002 | Menz et al. |
| 2002/0129820 A1 | 9/2002 | Ryan et al. |
| 2002/0133183 A1 | 9/2002 | Lentz et al. |
| 2002/0133226 A1 | 9/2002 | Marquez et al. |
| 2002/0138138 A1 | 9/2002 | Yang |
| 2002/0151970 A1 | 10/2002 | Garrison et al. |
| 2002/0161377 A1 | 10/2002 | Rabkin |
| 2002/0161392 A1 | 10/2002 | Dubrul |
| 2002/0161394 A1 | 10/2002 | Macoviak et al. |
| 2002/0183839 A1 | 12/2002 | Garrison et al. |
| 2002/0193871 A1 | 12/2002 | Beyersdorf et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0036795 A1 | 2/2003 | Andersen et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0114913 A1 | 6/2003 | Spenser et al. |
| 2003/0125795 A1 | 7/2003 | Pavcnik et al. |
| 2003/0125805 A1 | 7/2003 | Johnson et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0163194 A1 | 8/2003 | Quijano et al. |
| 2003/0181850 A1 | 9/2003 | Diamond et al. |
| 2003/0191519 A1 | 10/2003 | Lombardi et al. |
| 2003/0191528 A1 | 10/2003 | Quijano et al. |
| 2003/0192164 A1 | 10/2003 | Austin |
| 2003/0199913 A1 | 10/2003 | Dubrul et al. |
| 2003/0199963 A1 | 10/2003 | Tower et al. |
| 2003/0208261 A1 | 11/2003 | Thorpe et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034407 A1 | 2/2004 | Sherry |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0055606 A1 | 3/2004 | Hendricksen et al. |
| 2004/0073301 A1 | 4/2004 | Donlon et al. |
| 2004/0078072 A1 | 4/2004 | Tu et al. |
| 2004/0078074 A1 | 4/2004 | Anderson et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0123437 A1 | 7/2004 | Kokish |
| 2004/0127979 A1 | 7/2004 | Wilson et al. |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson et al. |
| 2004/0167620 A1 | 8/2004 | Ortiz et al. |
| 2004/0186558 A1 | 9/2004 | Pavcnik et al. |
| 2004/0186563 A1 | 9/2004 | Lobbi |
| 2004/0193259 A1 | 9/2004 | Gabbay |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0225356 A1 | 11/2004 | Frater |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060029 A1 | 3/2005 | Le et al. |
| 2005/0060030 A1 | 3/2005 | Lashinski et al. |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075727 A1 | 4/2005 | Wheatley |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0107871 A1 | 5/2005 | Realyvasquez et al. |
| 2005/0113910 A1 | 5/2005 | Paniagua et al. |
| 2005/0119688 A1 | 6/2005 | Bergheim |
| 2005/0131438 A1 | 6/2005 | Cohn |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |

(56) References Cited

U.S. PATENT DOCUMENTS

| | | |
|---|---|---|
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0166389 A1 | 8/2005 | Perreault et al. |
| 2005/0187616 A1 | 8/2005 | Realyvasquez |
| 2005/0197695 A1 | 9/2005 | Stacchino et al. |
| 2005/0197696 A1 | 9/2005 | Duran |
| 2005/0203549 A1 | 9/2005 | Realyvasquez |
| 2005/0203605 A1 | 9/2005 | Dolan |
| 2005/0203618 A1 | 9/2005 | Sharkawy et al. |
| 2005/0222674 A1 | 10/2005 | Paine |
| 2005/0222675 A1 | 10/2005 | Sauter |
| 2005/0228495 A1 | 10/2005 | Macoviak |
| 2005/0229670 A1 | 10/2005 | Perreault |
| 2005/0234537 A1 | 10/2005 | Edin |
| 2005/0234546 A1 | 10/2005 | Nugent et al. |
| 2005/0240200 A1 | 10/2005 | Bergheim |
| 2005/0240256 A1 | 10/2005 | Austin |
| 2005/0240263 A1 | 10/2005 | Fogarty et al. |
| 2005/0261759 A1 | 11/2005 | Lambrecht et al. |
| 2005/0267529 A1 | 12/2005 | Crockett et al. |
| 2005/0283232 A1 | 12/2005 | Gabbay |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin et al. |
| 2006/0025855 A1 | 2/2006 | Lashinski et al. |
| 2006/0052867 A1 | 3/2006 | Revuelta et al. |
| 2006/0058775 A1 | 3/2006 | Stevens et al. |
| 2006/0058872 A1 | 3/2006 | Salahieh et al. |
| 2006/0074486 A1 | 4/2006 | Liddicoat et al. |
| 2006/0085060 A1 | 4/2006 | Campbell |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0190017 A1 | 8/2006 | Cyr et al. |
| 2006/0195134 A1 | 8/2006 | Crittenden |
| 2006/0195184 A1 | 8/2006 | Lane et al. |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0247763 A1 | 11/2006 | Slater |
| 2006/0253134 A1 | 11/2006 | Ortiz et al. |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0265855 A1 | 11/2006 | Stenzel |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0027534 A1 | 2/2007 | Bergheim et al. |
| 2007/0032850 A1 | 2/2007 | Ruiz et al. |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0056346 A1 | 3/2007 | Spenser et al. |
| 2007/0061009 A1 | 3/2007 | Spenser et al. |
| 2007/0073387 A1 | 3/2007 | Forster et al. |
| 2007/0073392 A1 | 3/2007 | Heyninck Jantz et al. |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0093890 A1 | 4/2007 | Eliasen et al. |
| 2007/0100356 A1 | 5/2007 | Lucatero et al. |
| 2007/0100432 A1 | 5/2007 | Case et al. |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0106372 A1 | 5/2007 | Osborne et al. |
| 2007/0112415 A1 | 5/2007 | Bartlett |
| 2007/0112422 A1 | 5/2007 | Dehdashtian |
| 2007/0118209 A1 | 5/2007 | Strecker |
| 2007/0118215 A1 | 5/2007 | Moaddeb |
| 2007/0142968 A1 | 6/2007 | Prisco et al. |
| 2007/0162102 A1 | 7/2007 | Ryan et al. |
| 2007/0162113 A1 | 7/2007 | Sharkawy et al. |
| 2007/0168024 A1 | 7/2007 | Khairkhahan |
| 2007/0173861 A1 | 7/2007 | Strommer et al. |
| 2007/0185513 A1 | 8/2007 | Woolfson et al. |
| 2007/0203391 A1 | 8/2007 | Bloom et al. |
| 2007/0203503 A1 | 8/2007 | Salahieh et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0237802 A1 | 10/2007 | McKay |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288000 A1 | 12/2007 | Bonan |
| 2007/0293942 A1 | 12/2007 | Mirzaee |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan et al. |
| 2008/0065001 A1 | 3/2008 | DiNucci et al. |
| 2008/0065011 A1 | 3/2008 | Marchand et al. |
| 2008/0065204 A1 | 3/2008 | Macoviak et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077234 A1 | 3/2008 | Styrc |
| 2008/0082164 A1 | 4/2008 | Friedman |
| 2008/0082165 A1 | 4/2008 | Wilson et al. |
| 2008/0082166 A1 | 4/2008 | Styrc et al. |

(56) References Cited

U.S. PATENT DOCUMENTS

| | | |
|---|---|---|
| 2008/0097595 A1 | 4/2008 | Gabbay |
| 2008/0103586 A1 | 5/2008 | Styrc et al. |
| 2008/0125859 A1 | 5/2008 | Salahieh et al. |
| 2008/0133033 A1 | 6/2008 | Wolff et al. |
| 2008/0140189 A1 | 6/2008 | Nguyen et al. |
| 2008/0147105 A1 | 6/2008 | Wilson et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188880 A1 | 8/2008 | Fischer et al. |
| 2008/0188928 A1 | 8/2008 | Salahieh et al. |
| 2008/0215143 A1 | 9/2008 | Seguin |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0249619 A1 | 10/2008 | Stacchino et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0255662 A1 | 10/2008 | Stacchino et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0018570 A1 | 1/2009 | Righini et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0157175 A1 | 6/2009 | Benichou |
| 2009/0164004 A1 | 6/2009 | Cohn |
| 2009/0164006 A1 | 6/2009 | Seguin et al. |
| 2009/0171447 A1 | 7/2009 | Von Segesser et al. |
| 2009/0171456 A1 | 7/2009 | Kveen et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0192603 A1 | 7/2009 | Ryan |
| 2009/0198316 A1 | 8/2009 | Laske et al. |
| 2009/0209955 A1 | 8/2009 | Forster et al. |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0222084 A1 | 9/2009 | Friedman |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0254165 A1 | 10/2009 | Tabor et al. |
| 2009/0287296 A1 | 11/2009 | Manasse |
| 2009/0287299 A1 | 11/2009 | Tabor et al. |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0249661 A1 | 9/2010 | Righini et al. |
| 2010/0256723 A1 | 10/2010 | Murray |
| 2010/0262043 A1 | 10/2010 | Sauter et al. |
| 2010/0274351 A1 | 10/2010 | Rolando et al. |
| 2010/0292782 A1 | 11/2010 | Giannetti et al. |
| 2011/0082539 A1 | 4/2011 | Suri |
| 2011/0288636 A1 | 11/2011 | Rolando et al. |
| 2012/0172982 A1 | 7/2012 | Stacchino et al. |
| 2013/0325112 A1 | 12/2013 | Stacchino et al. |
| 2013/0345800 A1 | 12/2013 | Stacchino et al. |
| 2014/0052244 A1 | 2/2014 | Rolando et al. |
| 2014/0350666 A1 | 11/2014 | Righini |
| 2015/0148895 A1 | 5/2015 | Stacchino et al. |

FOREIGN PATENT DOCUMENTS

| | | |
|---|---|---|
| DE | 19532846 A1 | 3/1997 |
| DE | 19546692 C2 | 6/1997 |
| DE | 29911694 U1 | 9/1999 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049815 A1 | 4/2002 |
| DE | 10121210 A1 | 11/2002 |
| DE | 10301026 A1 | 2/2004 |
| DE | 19857887 A1 | 5/2005 |
| DE | 102004019254 B3 | 11/2005 |
| EP | 0133420 B1 | 2/1988 |
| EP | 0155245 B1 | 5/1990 |
| EP | 0401199 B1 | 1/1995 |
| EP | 0592410 B1 | 10/1995 |
| EP | 0515324 B1 | 12/1996 |
| EP | 0850607 A1 | 7/1998 |
| EP | 1057460 A1 | 12/2000 |
| EP | 0778009 B1 | 7/2002 |
| EP | 1259194 B1 | 2/2005 |
| EP | 1214020 B1 | 3/2005 |
| EP | 1353420 B1 | 3/2005 |
| EP | 1088529 B1 | 6/2005 |
| EP | 1014896 B1 | 11/2005 |
| EP | 1469797 A1 | 11/2005 |
| EP | 1603493 A2 | 12/2005 |
| EP | 1174098 B1 | 3/2006 |
| EP | 1600127 B1 | 11/2006 |
| EP | 1255510 A1 | 4/2007 |
| EP | 1143882 B1 | 12/2007 |
| EP | 1913901 A1 | 4/2008 |
| EP | 1690515 B1 | 7/2008 |
| EP | 1570809 B1 | 1/2009 |
| EP | 1330213 B1 | 3/2009 |
| EP | 2047824 A1 | 4/2009 |
| EP | 2055266 A2 | 5/2009 |
| EP | 1370201 B1 | 9/2009 |
| EP | 2119417 A2 | 11/2009 |
| EP | 2133039 A2 | 12/2009 |
| FR | 2788217 A1 | 7/2000 |
| FR | 2815844 A1 | 1/2003 |
| GB | 2083362 A | 3/1982 |
| GB | 2056023 A | 8/1983 |
| GB | 2433700 A | 12/2007 |
| JP | 11332997 A | 12/1999 |
| NL | 1017275 C2 | 8/2002 |
| SU | 1271508 A1 | 11/1986 |
| WO | WO9209247 A1 | 6/1992 |
| WO | WO9529640 A1 | 11/1995 |
| WO | WO9639942 A1 | 12/1996 |
| WO | WO9724989 A1 | 7/1997 |
| WO | WO9814138 A1 | 4/1998 |
| WO | WO9817202 A1 | 4/1998 |
| WO | WO9829057 A1 | 7/1998 |
| WO | WO9913802 A1 | 3/1999 |
| WO | WO9953864 A1 | 10/1999 |
| WO | WO9955255 A1 | 11/1999 |
| WO | WO9956665 A1 | 11/1999 |

(56) References Cited

FOREIGN PATENT DOCUMENTS

| | | |
|---|---|---|
| WO | WO0006052 A1 | 2/2000 |
| WO | WO9953866 A1 | 2/2000 |
| WO | WO0021464 A1 | 4/2000 |
| WO | WO0030565 A1 | 6/2000 |
| WO | WO0041652 A1 | 7/2000 |
| WO | WO0044313 A1 | 8/2000 |
| WO | WO0047136 A1 | 8/2000 |
| WO | WO0047139 A1 | 8/2000 |
| WO | WO0062714 A1 | 10/2000 |
| WO | WO0062716 A1 | 10/2000 |
| WO | WO0121076 A1 | 3/2001 |
| WO | WO0121107 A1 | 3/2001 |
| WO | WO0135870 A1 | 5/2001 |
| WO | WO0149213 A2 | 7/2001 |
| WO | WO0154625 A1 | 8/2001 |
| WO | WO0162189 A1 | 8/2001 |
| WO | WO0164137 A1 | 9/2001 |
| WO | WO0176510 A2 | 10/2001 |
| WO | WO0211646 A1 | 2/2002 |
| WO | WO0222054 A1 | 3/2002 |
| WO | WO0236048 A1 | 5/2002 |
| WO | WO0121110 A1 | 8/2002 |
| WO | WO02041789 A2 | 8/2002 |
| WO | WO0121103 A2 | 10/2002 |
| WO | WO02076348 A1 | 10/2002 |
| WO | WO0292257 A1 | 11/2002 |
| WO | WO02047575 A2 | 12/2002 |
| WO | WO03003949 A2 | 1/2003 |
| WO | WO03011195 A2 | 2/2003 |
| WO | WO03047468 A1 | 6/2003 |
| WO | WO03003943 A2 | 11/2003 |
| WO | WO03094797 A1 | 11/2003 |
| WO | WO2004019825 A1 | 3/2004 |
| WO | WO2004082527 A2 | 9/2004 |
| WO | WO2004089250 A1 | 10/2004 |
| WO | WO2005004753 A1 | 1/2005 |
| WO | WO2004091455 A2 | 2/2005 |
| WO | WO2005046528 A1 | 5/2005 |
| WO | WO2005062980 A2 | 7/2005 |
| WO | WO2005082578 A1 | 9/2005 |
| WO | WO2006005015 A2 | 1/2006 |
| WO | WO2006026371 A1 | 3/2006 |
| WO | WO2006044679 A1 | 4/2006 |
| WO | WO2006086135 A2 | 8/2006 |
| WO | WO2006088712 A1 | 8/2006 |
| WO | WO2006093795 A1 | 9/2006 |
| WO | WO2006117016 A1 | 11/2006 |
| WO | WO2006124649 A2 | 11/2006 |
| WO | WO2006127089 A1 | 11/2006 |
| WO | WO2006127765 A1 | 11/2006 |
| WO | WO2006135831 A1 | 12/2006 |
| WO | WO2006136930 A1 | 12/2006 |
| WO | WO2007009117 A1 | 1/2007 |
| WO | WO2007053243 A2 | 5/2007 |
| WO | WO2007030825 A2 | 6/2007 |
| WO | WO2007071436 A2 | 6/2007 |
| WO | WO2007130537 A1 | 11/2007 |
| WO | WO2006007401 A2 | 1/2008 |
| WO | WO0121097 A2 | 3/2008 |
| WO | WO2008028569 A1 | 3/2008 |
| WO | WO2008035337 A2 | 3/2008 |
| WO | WO2008047354 A2 | 4/2008 |
| WO | WO2008070797 A2 | 6/2008 |
| WO | WO2008089365 A2 | 7/2008 |
| WO | WO2008138584 A1 | 11/2008 |
| WO | WO2008150529 A1 | 12/2008 |
| WO | WO2009002548 A1 | 12/2008 |
| WO | WO2009024716 A2 | 2/2009 |
| WO | WO2009029199 A1 | 3/2009 |
| WO | WO2009042196 A2 | 4/2009 |
| WO | WO2009045331 A1 | 4/2009 |
| WO | WO2009045338 A1 | 4/2009 |
| WO | WO2009061389 A2 | 5/2009 |
| WO | WO2009091509 A1 | 7/2009 |
| WO | WO2009094188 A2 | 7/2009 |
| WO | WO2009111241 A2 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. I 664-669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

(56) References Cited

OTHER PUBLICATIONS

Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Decision Rejecting Opposition dated Oct. 19, 2011, filed in EP Patent 1690515, 22 pages.
Definition of Hinge downloaded from Voculabulary.com, received at the EPO on Dec. 18, 2012, 1 page.
Definition of Hinge, downloaded from www.meriam-webster.com on Jan. 31, 2013, 3 pages.
Definition of Minimum, downloaded from www.meriam-webster.com on Jan. 31, 2013, 2 pages.
European Search Report issued in EP 10183557, mailed Apr. 11, 2011, 7 pages.
European Search Report issued in EP App No. 08165227, dated Mar. 13, 2009.
European Search Report issued in EP Application No. 05004289, dated Jun. 2, 2005, 3 pages.
European Search Report issued in EP Application No. 06101425, dated May 3, 2006, 6 pages.
European Search Report issued in EP Application No. 08150075, dated Mar. 27, 2008, 6 pages.
European Search Report issued in EP Application No. 11425029, dated Aug. 17, 2011, 5 pages.
European Search Report issued in EP Application No. 11425030, dated Aug. 10, 2011, 5 pages.
European Search Report issued in EP Publication No. 1570809 (EP App No. 05004289.4), dated Jan. 5, 2007, 5 pages.
Extended European Search Report issued in EP 09179414, dated Oct. 18, 2010, 8 pages.
Extended European Search Report issued in EP App No. 09158822, dated Sep. 29, 2009, 5 pages.
Hanzel, et al., "Complications of percutaneous aortic valve replacement: experience with the CriberEdwardsTm percutaneous heart valve," EuroIntervention Supplements (2006), I (Supplement A) A3-A8.
Huber, et al., "Do Valved Stents Compromise Coronary Flow?" Eur. J. Cardiothorac. Surg. 2004;25:754-759.
International Search Report and Written Opinion issued in PCT/IB2012/050604, mailed Jul. 26, 2012, 16 pages.
International Search Report and Written Opinion issued in PCT/IB2012/050608, mailed Jul. 24, 2012, 9 pages.
International Search Report issued in International Application No. PCT/IB2006/000967, published as WO2006/085225, mailed Jul. 6, 2006.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. 1V-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al., "Double-crowned valved stents for off-pump mitral valve replacement," European Journal of Cardio Thoracic Surgery, 28:194-198, 2005.
Medtech Insight, "New Frontiers in Heart Valve Disease," vol. 7, No. 8 (2005).
Minutes of the Oral Proceedings dated Oct. 19, 2011, filed in EP Patent 1690515, 4 pages.
Notice of Appeal dated Dec. 28, 2011 filed in EP Patent 1690515, 3 pages.
Notice of Opposition with Facts, Evidence and Arguments filed in EP Patent 1690515 dated Apr. 30, 2009, 21 pages.
Palacios, "Percutaneous Valve Replacement and Repair, Fiction or Reality?" Journal of American College of Cardiology, vol. 44, No. 8 (2004) pp. 1662-1663.
Pavcnik et al., "Aortic and venous valve for percutaneous insertion," Min. Invas. Ther. & Allied Techol. 2000, vol. 9, pas. 287-292.
Pelton et al., "Medical Uses of Nitinol," Materials Science Forum vols. 327-328, pp. 63-70 (2000).
Response dated Dec. 9, 2009 to the Notice of Opposition filed in EP Patent 1690515 by ATS Medical Inc., 25 pages.
Response dated Mar. 23, 2011 to Summons dated Sep. 16, 2010, filed in EP Patent 1690515, 21 pages.
Response dated Sep. 17, 2012 to Grounds for Appeal dated Feb. 29, 2012, filed in EP Patent 1690515, 48 pages.
Response dated Sep. 17, 2012, Attachment A.
Response dated Sep. 17, 2012, Attachment B.
Roth, Mark, "Old metal heart valve did its job for 42 years", Pittsburgh Post-Gazette, Wednesday Mar. 5, 2008, 3 pages.
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Stassano et al., "Mid-term results of the valve-on-valve technique for bioprosthetic failure," Eur. J. Cardiothorac. Surg. 2000; 18:453-457.
Statement of Grounds for Appeal dated Feb. 29, 2012, filed in EP Patent 1690515, 41 pages.
Summons dated Apr. 15, 2013 with Facts and Submissions to Date to Attend Oral Proceedings on Nov. 5, 2013, filed in EP Patent 1690515, 13 pages.
Summons dated Sep. 16, 2010 with Facts and Submissions to Date, filed in EP Patent 1690515, 20 pages.
Webb, et al., "Percutaneous Aortic Valve Implantation Retrograde from the Femoral Artery," Circulation (2006), 1 13;842-850.
Grube, Eberhard et al., Case Report entitled "First Report on a Human Percutaneous Transluminal Implantation of a Self-Expanding Valve Prosthesis for Interventional Treatment of Aortic Valve Stenosis", Valvular Heart Disease, Catheterization and Cardiovascular Interventions, 2005, 66:465-469.
EP Communication issued in EP 07112385 on Jul. 30, 2009.
Extended European Search Report issued in EP 07106697, mailed Aug. 21, 2007, 6 pp.
Extended European Search Report issued in EP 07112385, mailed Apr. 1, 2008, 11 pp.
Extended European Search Report issued in EP 10168449, dated Aug. 19, 2010, 3 pages.
International Search Report and Written Opinion issued in PCT/US2010/028873, dated Jun. 15, 2010, 11 pages.
Partial European Search Report issued in EP 07112385, mailed Jan. 4, 2008, 5 pages.

\* cited by examiner

FIG. 13
FIG. 14
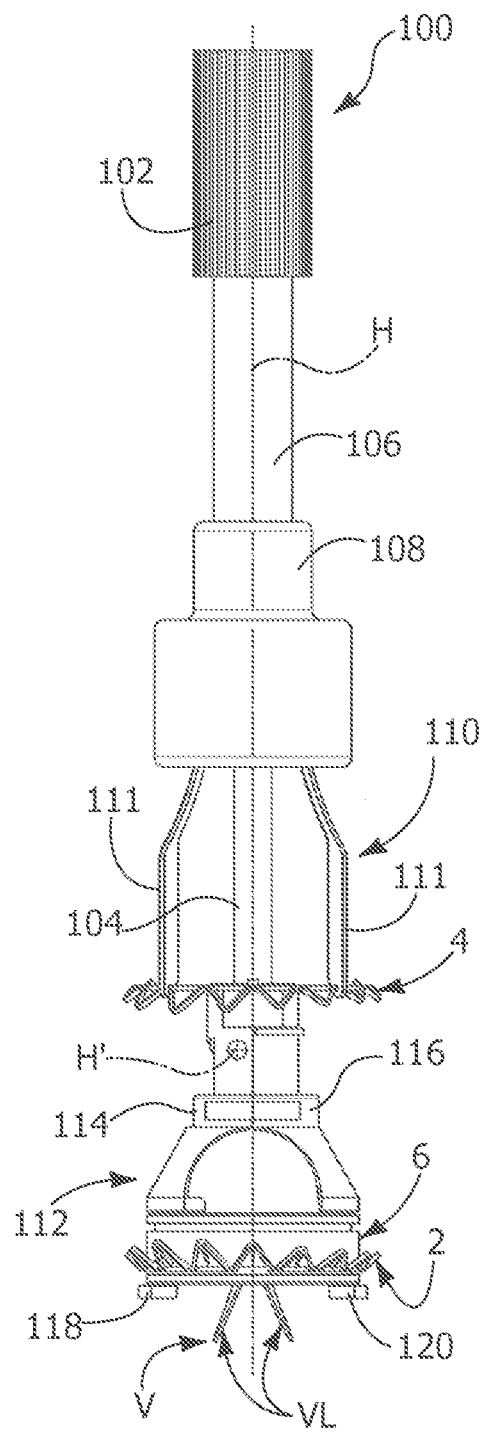
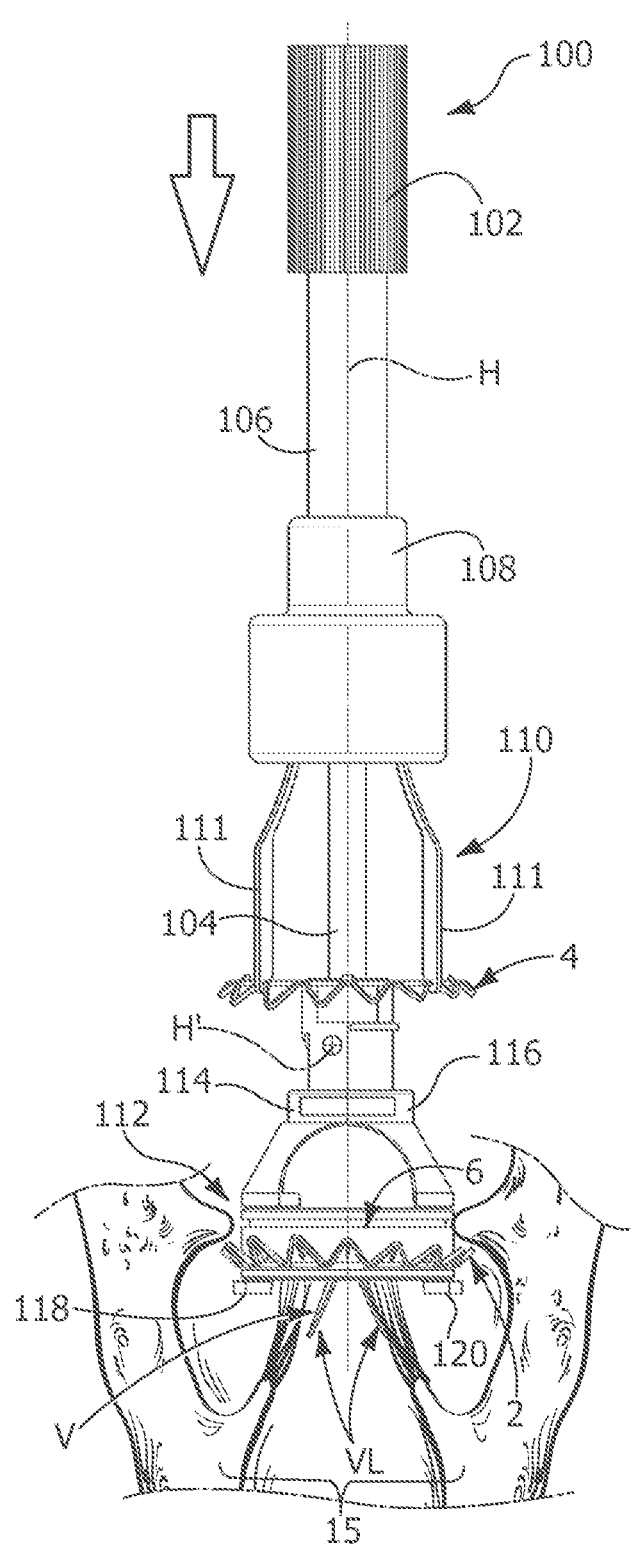

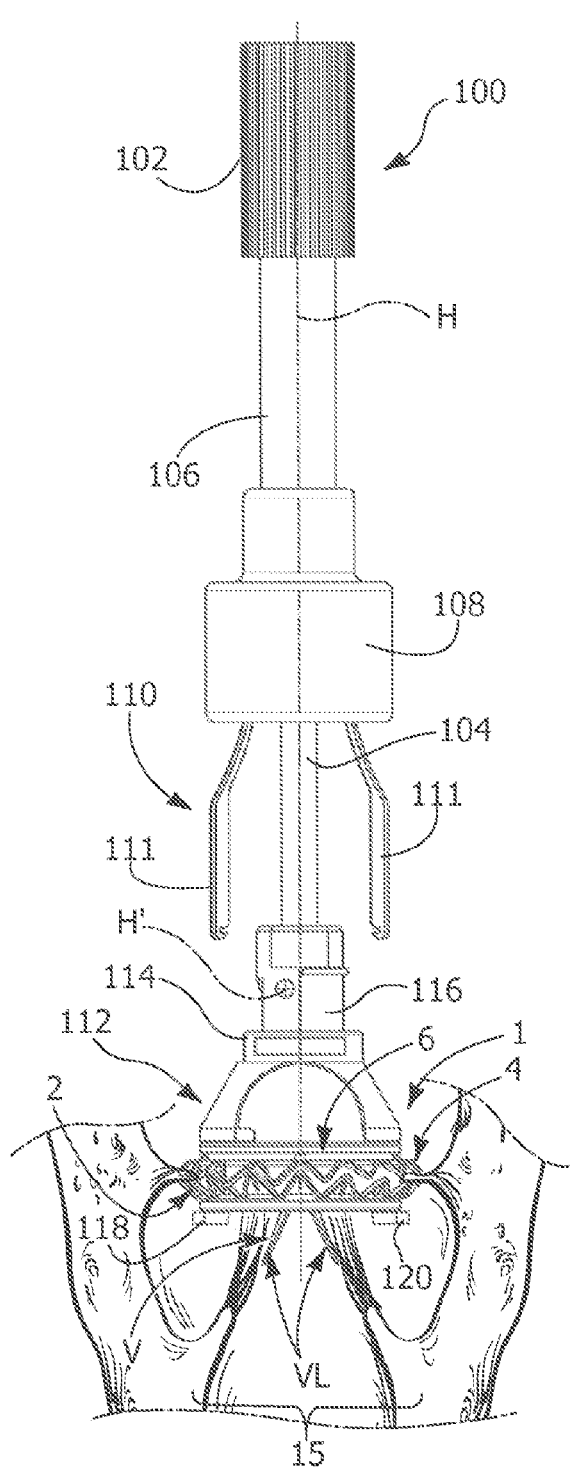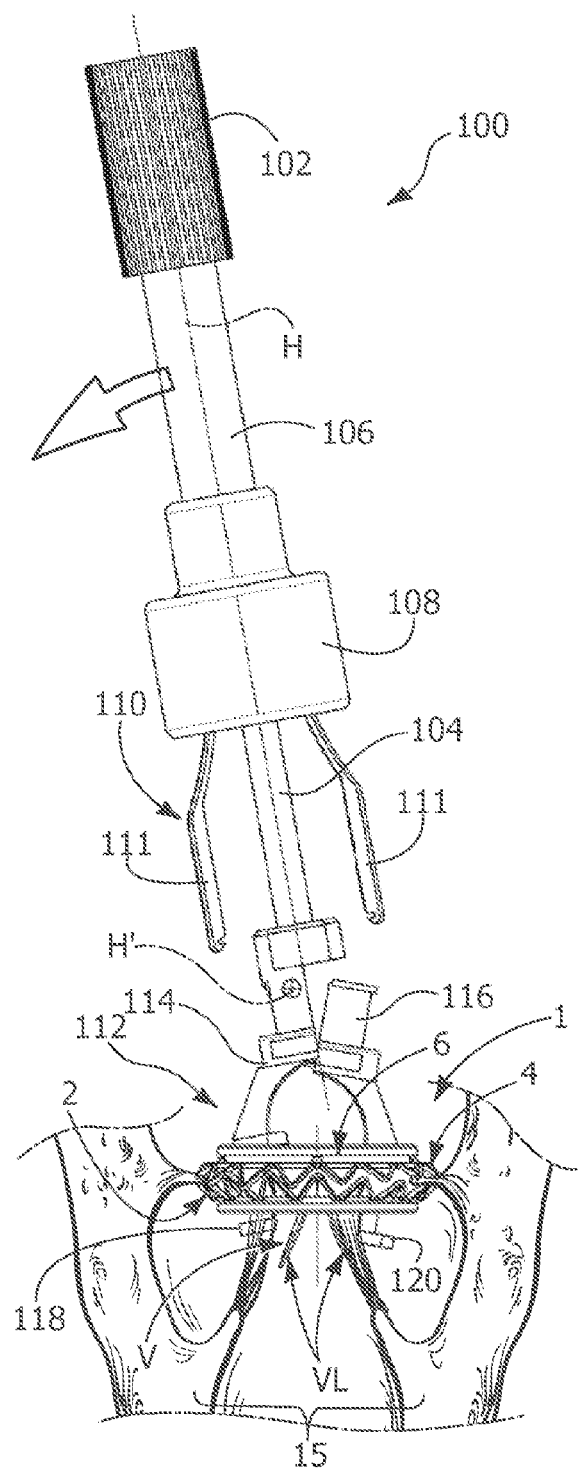

SUTURELESS ANCHORING DEVICE FOR CARDIAC VALVE PROSTHESES

CROSS-REFERENCE TO RELATED APPLICATION

This application is a national phase application of PCT Application No. PCT/IB2012/050608, internationally filed Feb. 10, 2012, which claims priority to European Application No. 11425030.1, filed Feb. 14, 2011, both of which are herein incorporated by reference in their entirety.

TECHNICAL FIELD

The present description relates to cardiac valve prostheses adapted for sutureless anchoring, anchoring systems for use with cardiac valve prostheses, and techniques and instruments for anchoring cardiac valve prostheses to an implantation site.

Exemplary cardiac valve prostheses may be prostheses for the replacement of the mitral valve or the aortic valve of the heart.

BACKGROUND

Anchoring a prosthesis to its implantation site may play a key role in implanting cardiac valve prostheses.

Implantation performed in an easy and rapid manner may reduce the risks related to procedures that are complex and/or long to perform.

U.S. Pat. No. 3,143,742, U.S. Pat. No. 3,546,710, U.S. Pat. No. 3,574,865 and U.S. Pat. No. 6,059,827 are representative of so-called sutureless cardiac valve prostheses, which are adapted for anchoring at the implantation site by a technique that does not require suturing the valve to the implantation site.

Once implanted, the valve must resist displacement with respect to the implantation site.

Displacement of the valve may occur, for example, as a consequence of the hydraulic pressure/thrust exerted by the blood flow or due to the movements of the beating heart.

SUMMARY

An object of the invention is to avoid the technical drawbacks previously described.

According to the invention, that object is achieved by means of a device having the features set forth in the annexed claims.

The claims form an integral part of the technical disclosure provided herein in relation to the invention.

BRIEF DESCRIPTION OF THE FIGURES

The invention will now be described purely by way of non-limiting example with reference to the annexed figures.

FIG. 8A illustrates an embodiment of an anchoring device, while

FIG. 10A is a detailed view according to arrow X of FIG. 8B, while

FIGS. 13 to 19 illustrate a sequence of implanting a cardiac valve prosthesis with an anchoring device according to various embodiments.

DETAILED DESCRIPTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment are included in at least one embodiment. Thus, the appearances of the phrases "in one embodiment" or "in an embodiment" in various places throughout this specification may be not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

While many of the following exemplary embodiments are shown and described with reference to repair of a mitral valve, the skilled artisan will recognize that many of these embodiments may also be used to repair or replace other heart valves.

Figure 1A:
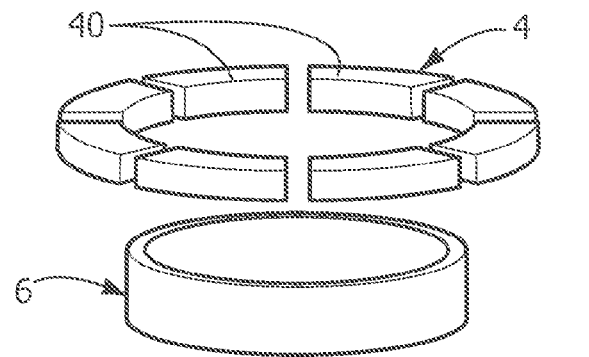
FIGS. 1A-C illustrate various embodiments of an anchoring device for cardiac valve prostheses.

In FIG. 1A, reference number 1 designates as a whole an anchoring device for anchoring a cardiac valve prosthesis to an implantation site, the anchoring device 1 including a first anchoring assembly 2, a second anchoring assembly 4 and a connection structure 6, arranged to operatively couple the first and the second anchoring assemblies 2, 4.

In various embodiments, the above mentioned components may be coaxial with respect to a longitudinal axis X of the device 1. The connection structure 6 may be configured for housing a cardiac valve prosthesis V, such as a cardiac valve prosthesis of the mechanical type with one or more artificial valve elements VL (see, e.g., FIGS. 2A, 2B, 2D, 8, 12A to 12D, and 13 to 19). Such prostheses are known in the art, which makes it unnecessary to provide a detailed description herein.

In various embodiments, an artificial cardiac valve prosthesis may include an annular element O defining an orifice of the prosthesis V wherein blood flow is regulated by means one or more artificial valve leaflets. According to exemplary embodiments, these valve leaflets are formed from biological tissue or from mechanical structures (e.g., two hemi-discs or semi-circular discs).

In various embodiments, the connection structure 6 may be a ring which defines an annular element (armature or stent) O of the prosthesis V, and may be thus part of the prosthesis V, with the artificial valve leaflets installed directly within the connection structure 6.

In various embodiments, the connection structure 6 may be configured substantially as a seat for the prosthesis V, whose annular element O may be received and fixed within the connection structure 6.

In various embodiments, the valve prosthesis V may be a biological prosthetic valve including one or more (e.g., three) leaflets made of biological tissue stitched together to reproduce the arrangement of the natural valve leaflets.

In various embodiments, the biological prosthesis may be received within the connection structure 6.

In various embodiments, the anchoring assemblies 2, 4 may be physically distinct with respect to the connection structure 6.

In various embodiments, one of the two anchoring assembly may be provided integral with the connection structure 6.

Figure 1B:
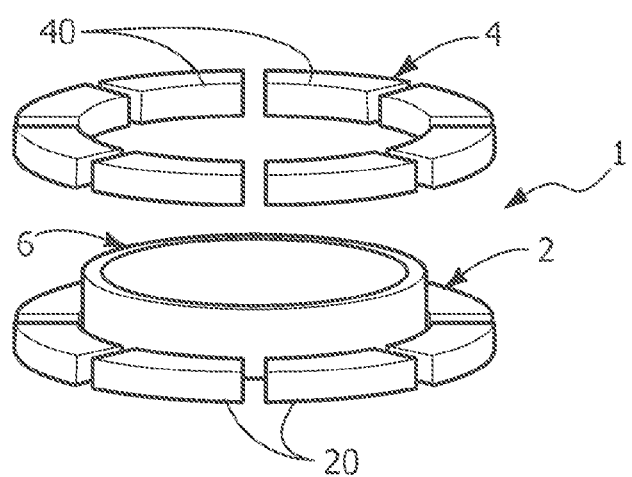

In various embodiments, as exemplified in FIG. 1B, the first anchoring assembly 2 may be provided integral with the connection structure 6, while the second anchoring assembly 4 may be provided as a separate element.

Figure 1C:
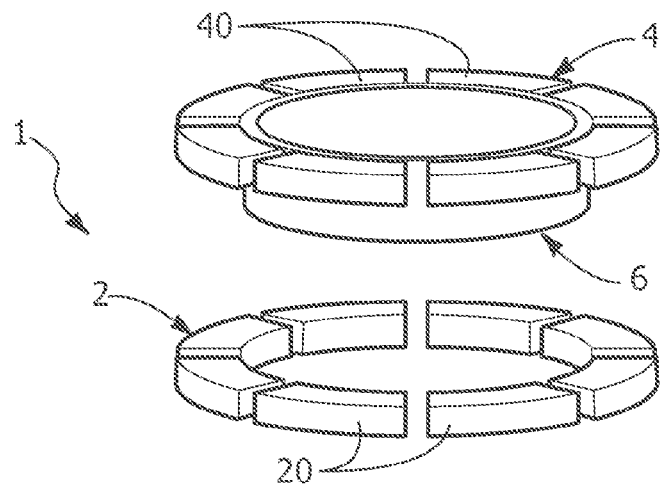

In various embodiments, as exemplified in FIG. 1C, the second anchoring assembly 4 may be provided integral with the connection structure 6, while the first anchoring assembly 2 may be provided as a separate element.

In various embodiments, while physically distinct from the connection structure 6, one of the two anchoring assemblies 2, 4, may be provided pre-installed thereon, the resulting arrangement thus being similar to embodiments wherein one anchoring assembly may be integral with the connection structure 6.

The schematic illustration of the anchoring assemblies 2, 4 of FIGS. 1A-C shows that in various embodiments these assemblies may include respective anchoring formations defining an annular, possibly non-continuous structure.

In various embodiments, the anchoring assemblies 2, 4 may be configured as a closed, continuous structure.

In various embodiments, either or both of the anchoring assemblies 2, 4 may be discontinuous, e.g., provided as a pair of tapered hemi-rings 8, 10 and 12, 14 respectively.

Figure 2A:
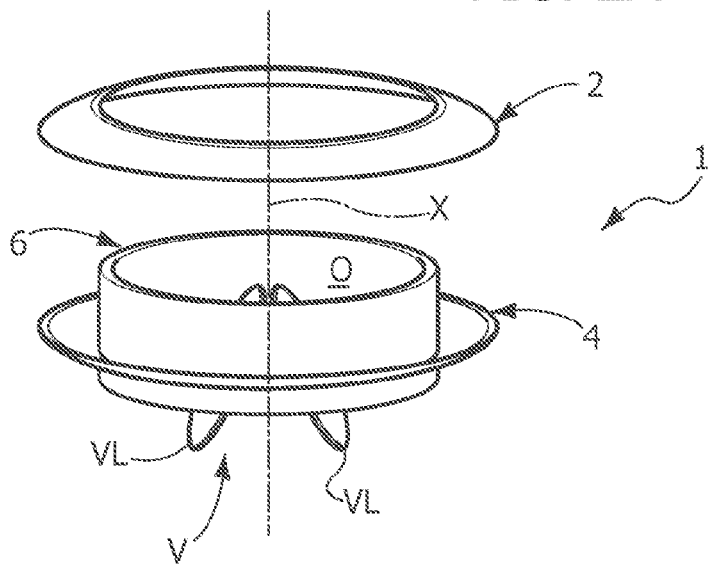
FIGS. 2A-2D illustrate various embodiments of an anchoring device for cardiac valve prostheses.
Figure 2B:
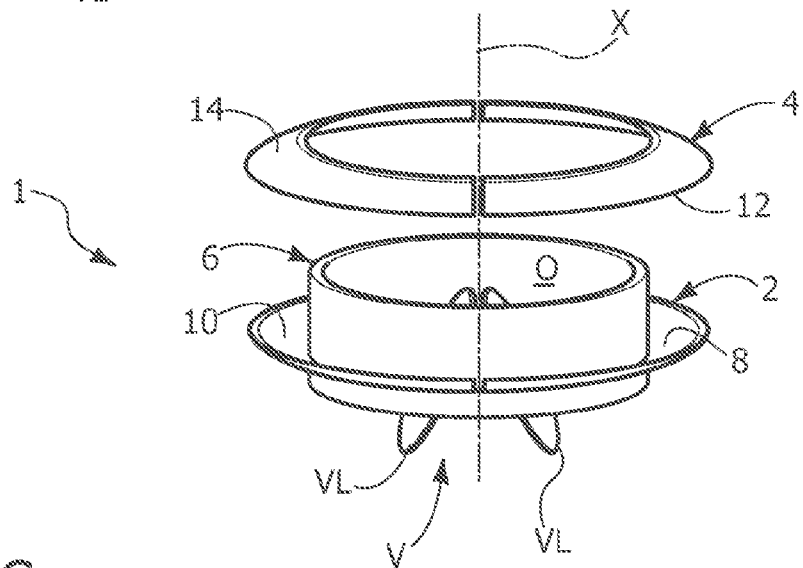

In various embodiments, as exemplified in FIG. 2A, the anchoring assemblies 2, 4 may be each provided as a closed tapered ring (such a structure that can be at least roughly assimilated to a Belleville spring), the two anchoring assemblies being arranged with their respective flared portions facing each other.

Figure 2C:
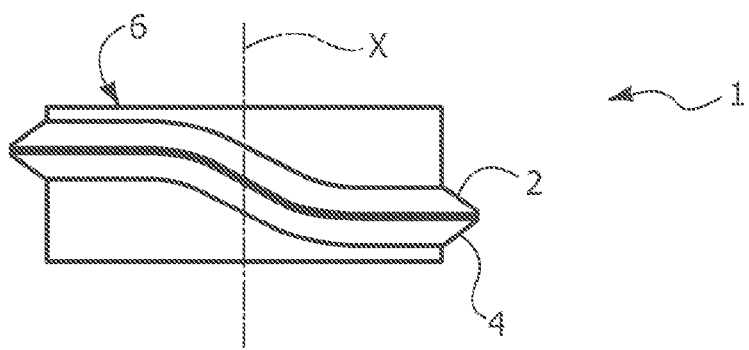
Figure 2D:
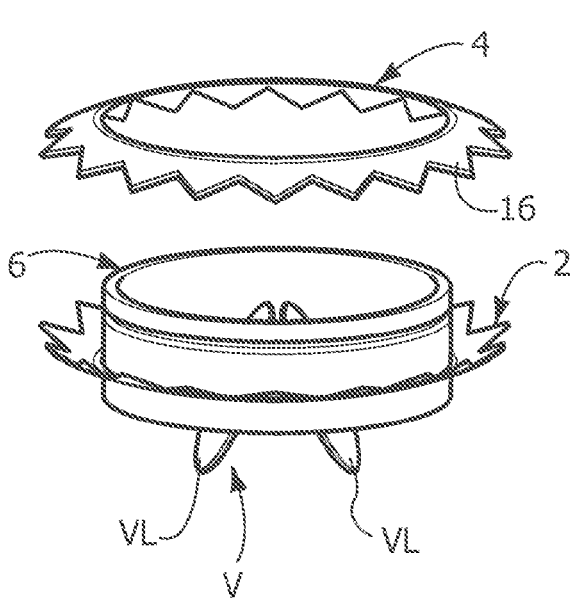

In various embodiments, as exemplified in FIG. 2C, either or both of the anchoring assemblies 2, 4 may have a tapered shape similar to that shown in FIG. 2A, and develop along a non-planar closed path.

In various embodiments, the anchoring assemblies 2, 4 may be provided as tapered rings with a plurality of radial anchoring formations 16.

In various embodiments, the anchoring formations are arranged in one or more pairs of complementary portions 20, 40, associated with the anchoring assemblies 2, 4, respectively. According to various embodiments, the complementary portions 20, 40 are arched portions associated with corresponding or complementary portions of the circumference of the anchoring assemblies.

In various embodiments, the anchoring formations 16 are configured as integral extensions of the corresponding anchoring assemblies.

In various embodiments, as exemplified in FIGS. 3A to 3D, the anchoring assemblies 2, 4 may have a variety of different structures.

Figure 3A:
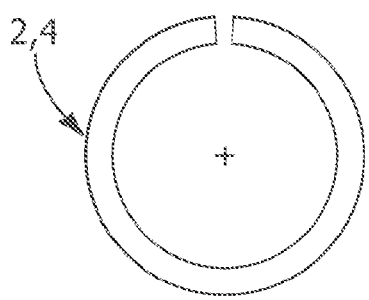
FIGS. 3A-D illustrate various embodiments of components of an anchoring device.
Figure 3B:
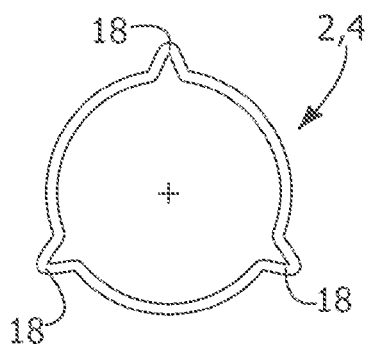

In various embodiments, as exemplified in FIG. 3A, either or both of the anchoring assemblies 2, 4 may be configured as an open annular element. Such a structure will exhibit a certain degree of circumferential deformability.

In various embodiments, either or both of the anchoring assemblies 2, 4 may be configured as closed annular elements including at least one recess shaped portion 18 that provides a certain deformability, i.e., either or both the anchoring assemblies 2, 4 may be configured as expandable closed rings.

In various embodiments, regardless their structure (i.e., open or closed), either or both of the anchoring assemblies 2, 4 may be provided with one or more inner radial teeth 19.

In various embodiments, the anchoring formations of each arched portion may be bent towards the complementary arched portion.

In various embodiments, these anchoring formations are substantially saw-tooth shaped.

Figure 4:
FIG. 4 illustrates an embodiment of an anchoring device coupled to an implant site.

In various embodiments, as exemplified in FIG. 4, the anchoring device 1 may be configured to provide a firm anchoring of a cardiac valve prosthesis to an implantation site without suture being required.

Such anchoring may be achieved in various embodiments by securing (e.g., capturing, sandwiching or pinching) portions of native biological tissue of the implantation site between the anchoring assemblies 2, 4. The native biological tissue may be pinched between the anchoring assemblies 2, 4 as they are coupled together for example by means of the connection structure 6.

In various embodiments, the implantation site may be the mitral valve annulus.

Figure 5A:
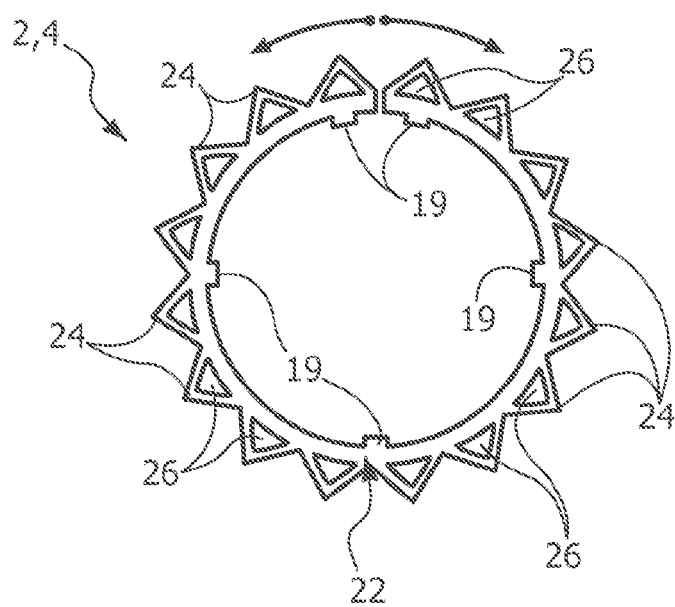
FIGS. 5A-B illustrate embodiments of the components shown in FIG. 3.

In various embodiments, as exemplified in FIG. 5A, either or both the anchoring assemblies 2, 4 may include a base body such as an open annular element 22 (similar to those of the embodiments of FIGS. 3A, 3C) having, extending radially outwardly therefrom, a crown of anchoring formations 24 having a saw-tooth profile similar to that of the anchoring formations 16 but each provided with an aperture 26, e.g., triangular in shape.

In various embodiments, at least some of the anchoring formations 24 may not have such apertures, thereby having a solid configuration more similar to that of the anchoring formations 16.

In various embodiments, the anchoring formations 24 are configured as integral extensions of the corresponding anchoring assemblies.

In various embodiments, teeth 19 may be provided in the base body 22, e.g. internally thereof.

In various embodiments, the anchoring formations 24 may have different radial extensions along the ring 8.

Figure 5B:
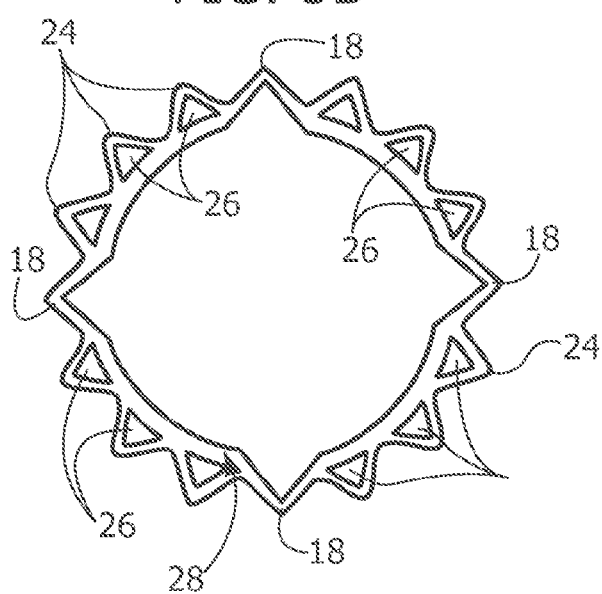

In various embodiments, as exemplified in FIG. 5B, either of both of the anchoring assemblies 2, 4 may include a base body such as a closed annular element 28 (similar to those of the embodiments of FIGS. 3B, 3D) and a plurality of anchoring formations 24, possibly provided with openings 26, arranged in groups alternate to the recess-shaped portions 18.

In various embodiments, the anchoring formations 24 (whether provided with the triangular openings 26 or not)

may be arranged to confer a substantially tapered shape to the anchoring assemblies 2, 4. That is, the anchoring formations 24 (as well as, in various embodiments, the recess-shaped portions 18) may be arranged so as to lie substantially at an angle with respect to the plane of the respective base body 22, 28.

In various embodiments, in correspondence with at least one pair of complementary arched portions having anchoring formations for anchoring on said native biological tissue located at or near the valve annulus, the anchoring formations include integral extensions of the anchoring assemblies 2, 4 extending radially outwardly of one of the anchoring assemblies in an alternate arrangement with respect to corresponding extensions extending radially outwardly of the other anchoring assembly. In various embodiments, these corresponding extensions may be similar or generally homologous to each other. Each anchoring formation of one anchoring assembly 2, 4 may thus be located, when the anchoring assemblies are coupled by the connection structure 6, between two adjacent formations of the other anchoring assembly, whereby the anchoring formations of the two anchoring assemblies, once coupled, give rise to an interdigitated (i.e., intertwined or intermingled) arrangement. That is, with the anchoring assemblies 2, 4 mutually coupled to secure the biological tissue, the extensions in the two complementary arched portions interdigitate and impart to the biological tissue secured therebetween a serpentine trajectory.

This may improve the stability of the anchoring device at the implantation site because the biological tissue at the implantation site may become trapped and pinched between the anchoring assemblies 2, 4 thus being tensioned, stretched and firmly held.

In various embodiments, the anchoring formations 24 (irrespective of whether solid or apertured) may be elastically deformable.

In various embodiments, the connection structure 6 may be a ring element including one or more coupling profiles adapted to receive the anchoring assemblies 2, 4.

Figure 6:
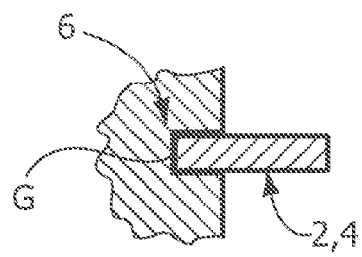
FIG. 6 is a partial sectional view of an embodiment of an anchoring device.

In various embodiments, as exemplified in FIG. 6, such coupling profiles may include annular grooves G, e.g., with a groove G for each anchoring assembly 2, 4.

In various embodiments, wherein the anchoring assemblies include radial teeth 19, only one assembly 2, 4 may be configured to engage within the groove G. In various embodiments, without the teeth 19, an annular portion of the base body may engage the groove G.

In various embodiments, at least one anchoring assembly may be configured as a closed annular element (e.g., as exemplified in FIGS. 2A, 2C, 2D, 3B, 3D, 5B) and that anchoring assembly may be coupled with the connection structure 6 (e.g., by snap-engagement) within a corresponding groove G by means of an elastic and, possibly, an additional plastic deformation of the anchoring assembly (which may be facilitated by the recess shaped portions 18, where present).

Figure 3C:
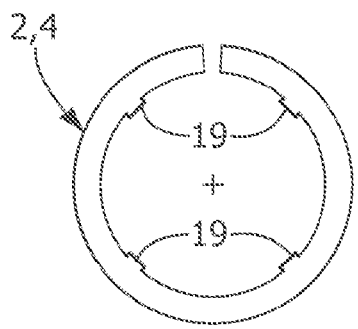
Figure 3D:
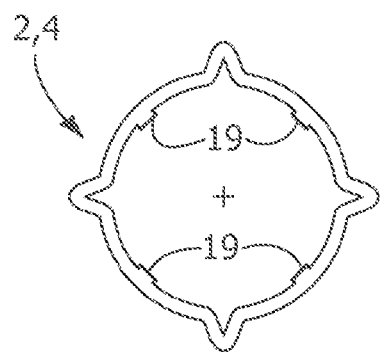

In various embodiments, at least one anchoring assembly may be configured as an open annular element (e.g., as exemplified in FIGS. 3A, 3C, 5A). Such an anchoring assembly may be coupled with the connection structure 6 by radially expanding it by moving apart the free ends thereof, by engaging the inner rim of the radially expanded anchoring assembly within a corresponding annular groove G and then letting the anchoring assembly contract again elastically so that the inner rim thereof is captured in the annular groove G.

In various embodiments, the anchoring formations may extend over different radial lengths around the outline of the corresponding base body.

Figure 7:
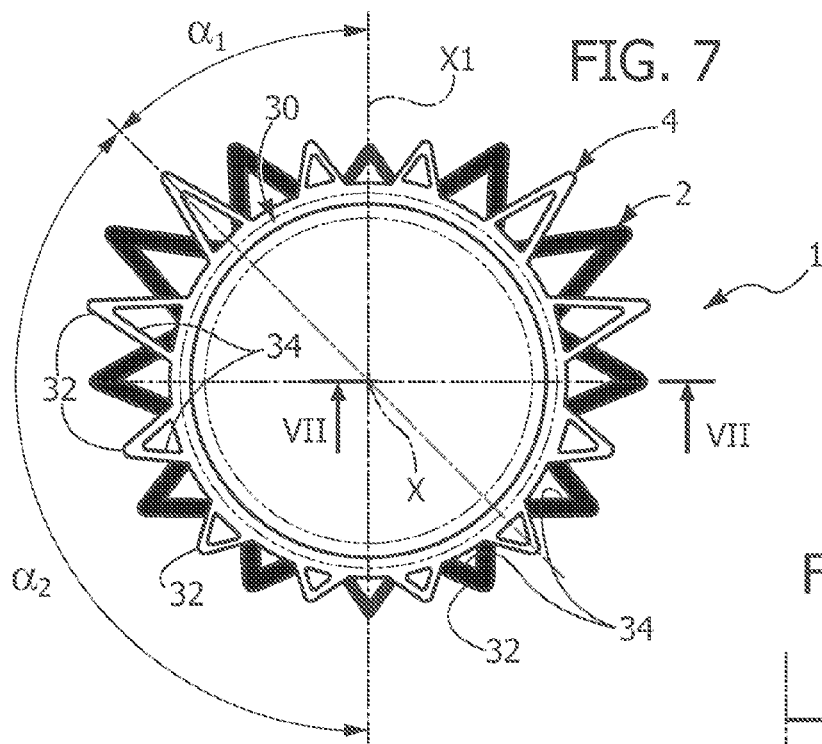
FIG. 7 illustrates embodiments of an anchoring device, with FIG. 7A being a sectional view along line VII-VII of FIG. 7.

In various embodiments, as exemplified in FIG. 7, either or both the anchoring assemblies 2, 4 may include a base body such as an annular element 30 (either open or closed), having a plurality of anchoring formations 32 extending radially outwardly therefrom.

In various embodiments, the anchoring formations 32 may be configured as integral extensions of the corresponding anchoring assemblies.

In various embodiments, the formations 32 may be substantially saw-tooth shaped and/or provided with (e.g., triangular) apertures 34.

In various embodiments, at least part of the anchoring formations 32 may not have a corresponding triangular aperture 34. In various embodiments, the anchoring assemblies 2, 4 may be provided with the teeth 19.

In various embodiments, the anchoring formations 34 may form an angle with respect to the plane base body so as to confer an overall tapered shape to the anchoring assembly to which they belong.

In various embodiments, the anchoring formations 32 (irrespective of whether solid or apertured) may be elastically deformable.

In various embodiments, each of the anchoring assemblies 2, 4 may be symmetrical with respect to a transverse axis X1 ("transverse" being in a direction substantially lying in the plane of the closed annular element 30 and orthogonal to the longitudinal axis X) and the anchoring formations 34 may have their radial extension increasing over a first angle $\alpha_1$ and then decreasing over a second angle $\alpha_2$, wherein the sum of the angles $\alpha_1 + \alpha_2$ may be equal to 180°. This may confer to the corresponding anchoring assembly 2, 4 (or both) a substantially D-shaped outline (in plan view), which renders the anchoring device 1 more easily adaptable to implantation sites such as, for example, the mitral valve annulus.

In various embodiments, the sum of the angles $\alpha_1 + \alpha_2$ may be equal to 120°, so that three groups of anchoring formations, each extending over 120°, may be provided on the anchoring assemblies and confer thereto a substantially three-lobed outline (in plan view), which renders the anchoring device 1 more easily adaptable to implantation sites such as, for example, the pulmonary valve annulus or the tricuspid valve annulus.

In various embodiments, adjacent anchoring formations 32 may be angularly spaced from each other thereby defining a crown of angular gaps.

Figure 7A:
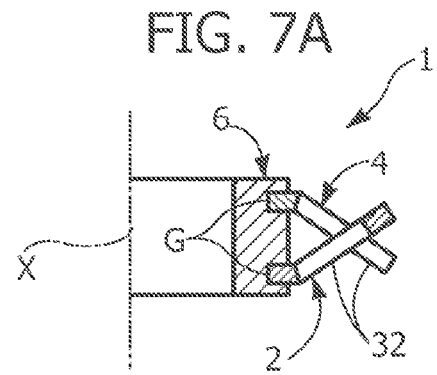
Figure 8A:
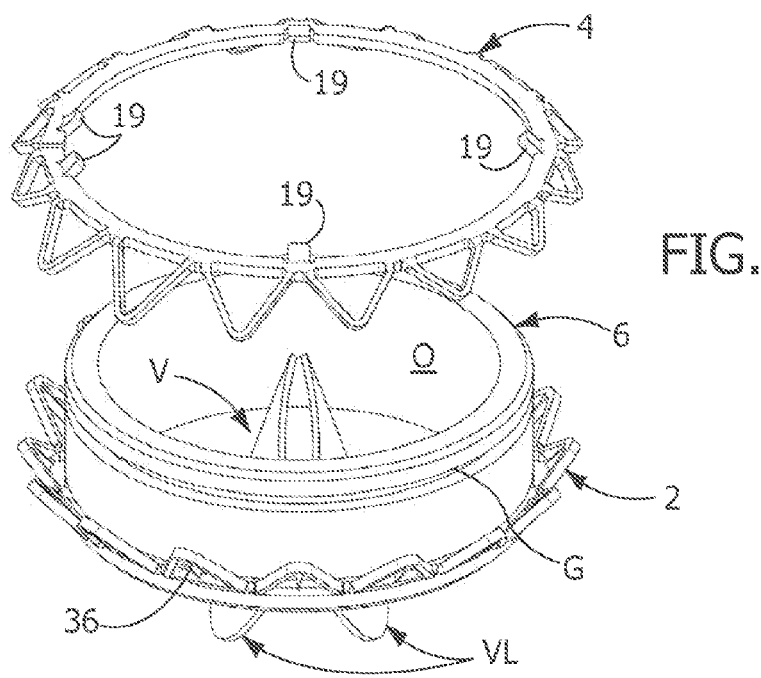
Figure 8B:
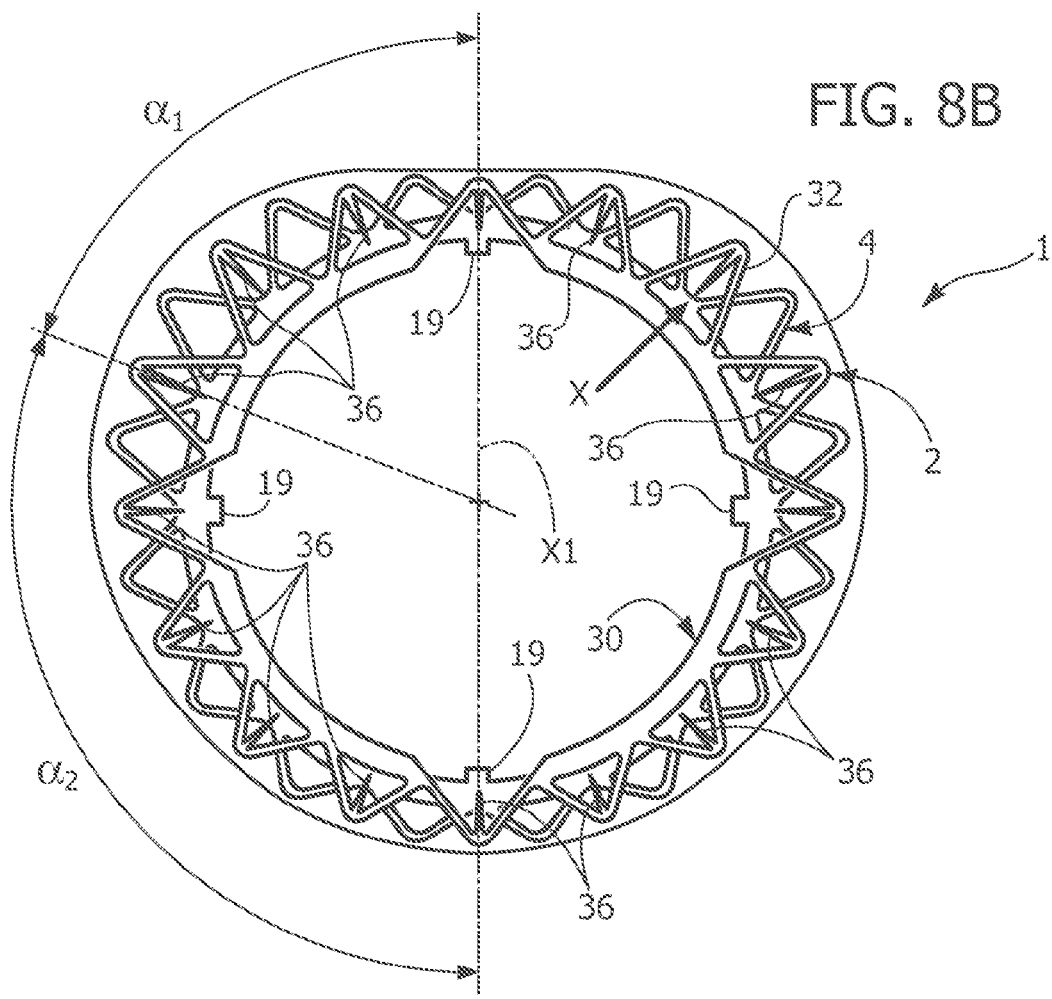
FIG. 8B is a plan view of an embodiment of an anchoring device with some parts removed for the sake of clarity.
Figure 10A:
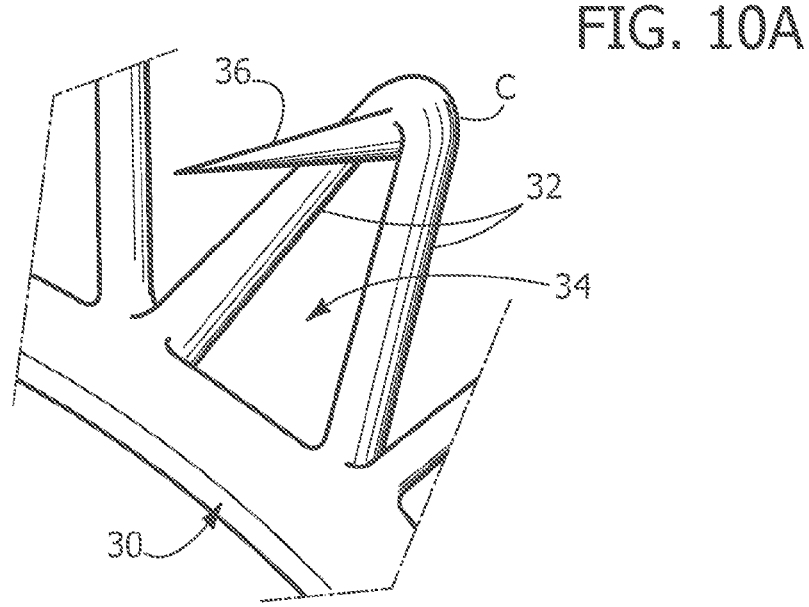

In various embodiments as exemplified in FIGS. 7 and 7A, these angular gaps may provide a sort of interpenetration (i.e., intertwining) of the anchoring assemblies 2, 4. In other words, with reference to FIG. 7, at least one pair of complementary arched portions of the anchoring assemblies are configured according to the embodiments exemplified in FIG. 6, each anchoring formation 32 of one anchoring assembly will extend between two subsequent (and spaced apart) anchoring formations of the other anchoring assembly. The anchoring formation will thus interdigitate and impart to the native biological tissue secured (e.g., pinched) therebetween a substantially serpentine-like trajectory. Such serpentine-like trajectory may include, for example, subsequent sinusoidal-like portions having a length in the range between 2 mm and 15 mm. The term "length" associated to the sinusoidal-like trajectory is used herein to indicate the "wavelength" of such sinusoidal-like trajectory, namely the distance between the free ends (e.g., the vertices) of two subsequent anchoring formations of an anchoring assembly (which is in the range between 2 and 15 mm as well), which substantially corresponds to subsequent peaks/valleys of the biological tissue.

Figure 9A:
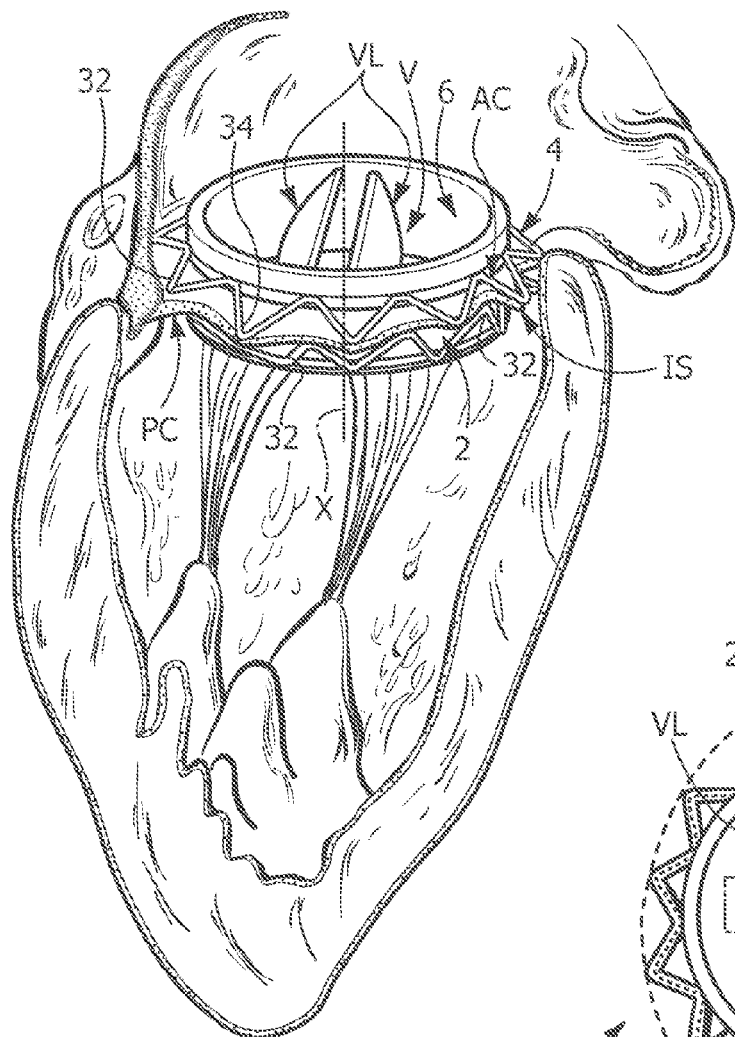
FIG. 9A is a perspective sectional view of an anchoring device according to various embodiments.
Figure 9B:
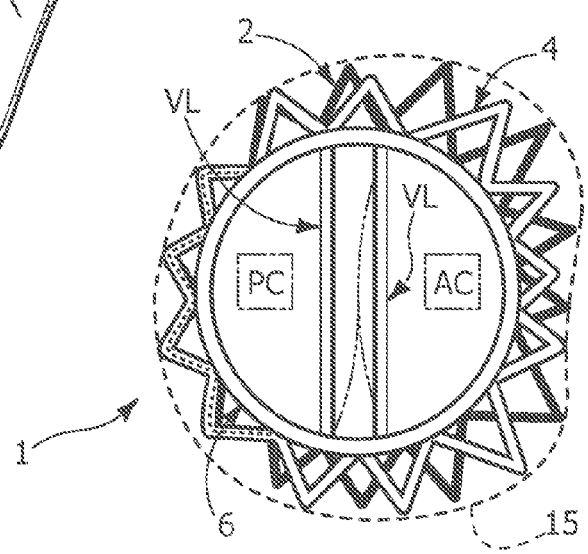
FIG. 9B is a plan view of an embodiment according to FIG. 9A.
Figure 9C:
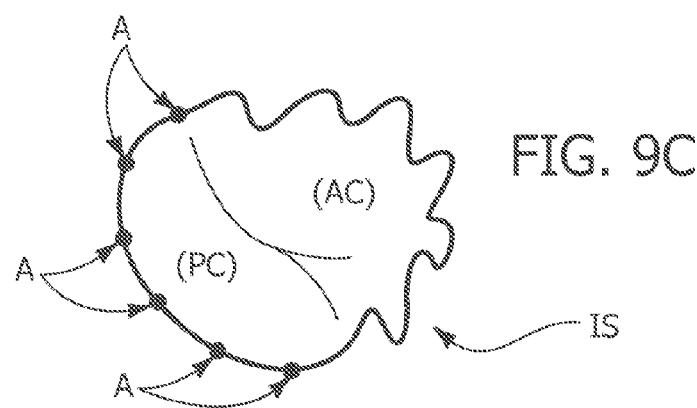
FIG. 9C is a schematic view of features of an anchoring device according to various embodiments.

With reference to FIGS. 9A, 9B, 9C, in various embodiments, the anchoring assemblies 2, 4 may be arranged so that at least one, preferably more than one, pair of anchoring formations 32 interdigitate and at least one, preferably more than one, pair of anchoring formations 32 form couples of co-operating extensions, i.e., they are substantially angularly aligned and do not interdigitate.

In various embodiments, the anchoring assemblies 2, 4 are configured so as to have a substantially D-shaped plan outline (as, for example, those exemplified in FIGS. 7, 8A, 8B, 9A, 9C) which allows a better adaptation to the mitral valve annulus. Also, the anchoring assemblies 2, 4 may be configured so that a group of anchoring formations 32 provided along a curved portion of such D-shaped outline (associated to a posterior cusp PC of the mitral valve) of each of the anchoring assemblies 2, 4 are arranged so as to be angularly aligned (i.e., they do not interdigitate) while another group of anchoring formations 32 provided along a straight portion of such D-shaped outline (associated to an anterior cusp AC of the mitral valve) of each anchoring assembly 2, 4 interdigitate.

This arrangement is exemplified in the embodiments shown in FIGS. 9A, 9B, wherein FIG. 9A shows a sectional view of the human heart and particularly of an implant site (that is, the mitral valve annulus). The view of the annulus is taken partly along a substantially curved trajectory so as to show the portions of biological tissue pinched between the anchoring assemblies 2, 4. The biological tissue pinched in the area of the anterior cusp AC has, therefore, a serpentine like trajectory, (FIGS. 9A, 9C), while the biological tissue pinched in the area of the posterior cusp PC has a substantially linear trajectory. With reference to FIG. 9C, in the area of the posterior cusp PC, the contact between the anchoring formations may be mainly localized in corresponding of contact areas A, while in the area of the anterior cusp AC the contact may be mainly distributed over the interdigitating anchoring formations 32. FIG. 9C shows a schematic representation of such condition.

According to various embodiments, in the area of the anterior cusp AC, the biological tissue, due to the annulus characteristics and surgical preparation of the implant site, offers a larger gripping area than that in the area of the posterior cusp PC. The anchoring assemblies/formations may be more rigid in correspondence with the anterior cusp (where the formations interdigitate), while they may be more elastic in correspondence of the posterior cusp PC (where the formations do not interdigitate and are deformed to compensate the different stiffness or thickness of the tissue in the area of the posterior cusp PC).

In various embodiments, the anchoring device 1 may include anchoring assemblies 2, 4 having different degrees of stiffness (i.e., one assembly stiffer than the other).

Various embodiments may adopt a degree of stiffness varying along (i.e., over the annular extension of) each anchoring assembly.

In various embodiments, as exemplified in FIG. 6 (or FIG. 9) anchoring formations having differentiated flexural stiffness (i.e., with respect to bending with respect to the plane of the base body) may be provided, that is, with adjacent or subsequent anchoring formations have different flexural stiffness. In various embodiments, however, the stiffness variation may be "step-wise", that is with the degree of stiffness variable over the anchoring assembly while being constant along certain portions thereof.

A differentiated degree of stiffness allows the anchoring assemblies to better adapt to the implantation site, e.g., to allow for the thickness of the biological tissue trapped between the anchoring assemblies 2, 4 being uneven due to the anatomy of the implantation site and/or the method used to trap the tissue. Such unevenness may be counterbalanced by a differentiated flexural stiffness of the anchoring formations, which can be rendered more flexible, e.g., in those areas where the biological tissue may be expected to be thicker.

In various embodiments, the flexural stiffness of the anchoring formations 24, 32 may be varied according to the anatomy of the implantation site: for example, as previously exemplified, the flexural stiffness of the anchoring formations may be differentiated on the basis of their locations with respect to the implantation site, that is depending on whether the anchoring formations are located at the anterior cusp or at the posterior cusp of the native mitral valve.

In various embodiments, as exemplified in FIGS. 8B and 10A-D, the anchoring formations 32 may be provided with tines or barbs 36.

In various embodiments, the tines or barbs 36 may protrude radially inwardly of the corresponding anchoring assembly and/or may be located substantially in correspondence of a vertex C of the corresponding anchoring formations 32.

In various embodiments, the tines or barbs 36 may protrude radially inwardly of the corresponding anchoring assembly in a plane different from the plane of the corresponding anchoring formation 32. In various embodiments, the tines or barbs 36 may protrude radially inwardly of the corresponding anchoring assembly in a substantially co-planar configuration with respect to the plane of the corresponding anchoring formation 32.

In various embodiments, as exemplified in FIG. 9, each anchoring formation 32 may be provided with a sting 36. In various embodiments, only some of the anchoring formations 32 may be provided with tines or barbs 36.

Figure 10B:
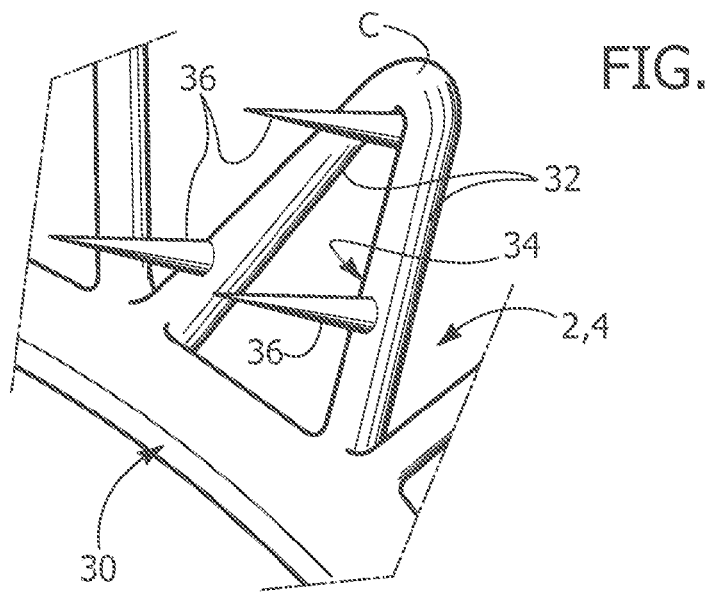
FIGS. 10B-D illustrate variants of the detail of FIG. 10A according to various embodiments.
Figure 10C:
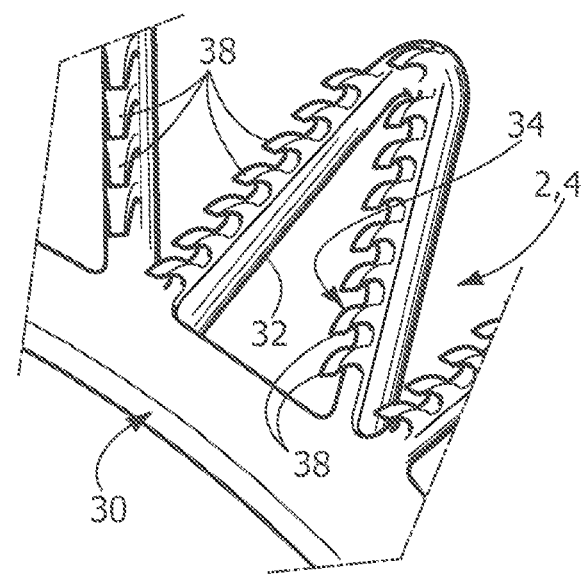
Figure 10D:
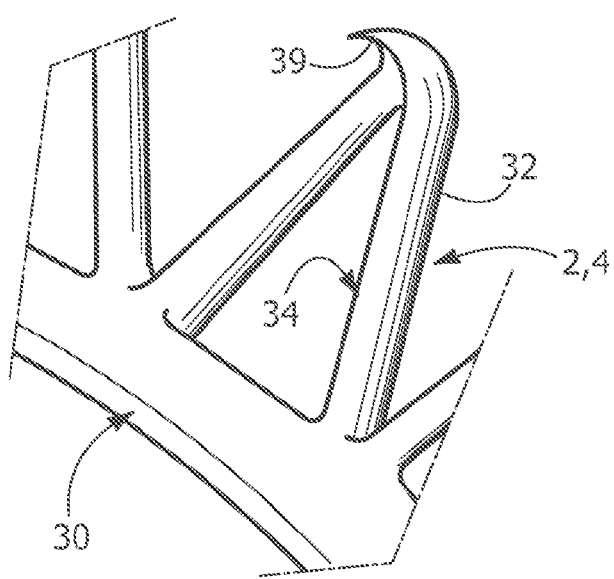

In various embodiments, as exemplified in FIGS. 10B-D, the arrangement of the tines or barbs 36 may be vary and/or the tines or barbs may be replaced with similar members.

In various embodiments, as exemplified in FIG. 10B, at least some of the anchoring formations 32 may be provided with more than one tine or barb 36, for example three tines or barbs arranged as the vertices of a triangle.

Irrespective of whether arranged in groups or singly on the anchoring formations 36, the tines or barbs may be configured to penetrate the biological tissue trapped between the anchoring assemblies 2, 4 thereby enhancing the stability of the anchoring device 1 at the implantation site.

In various embodiments, as exemplified in FIG. 10C, a plurality of saw-like teeth 38 may be provided around the outline of the anchoring formations 32 (i.e., along the struts surrounding the triangular aperture 34).

In various embodiments, as exemplified in FIG. 10D, a hook 39 may be provided at vertex C of at least some of the anchoring formations 32.

Both the teeth 38 and the hooks 39 may be configured to penetrate into the biological tissue at the implantation in order to improve the stability of the anchoring device at the implantation site.

In various embodiments, the arrangements and/or elements described above may be freely combined to meet specific needs, e.g., in the case of an implantation site requiring anchoring assemblies having different features at different locations.

Figure 11A:
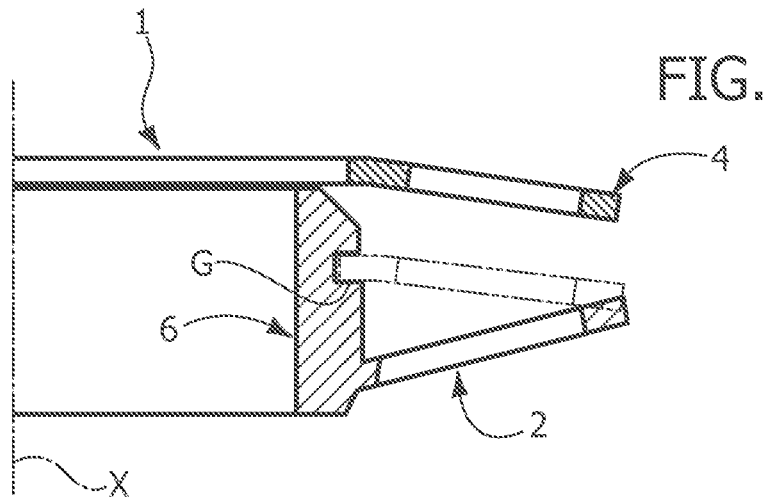
FIGS. 11A-C schematically show radial sections of embodiments of anchoring devices.
Figure 11B:
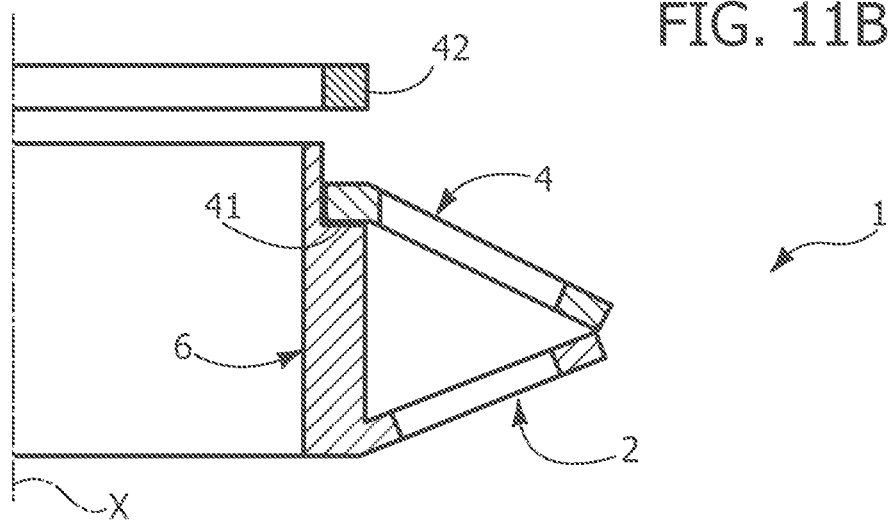
Figure 11C:
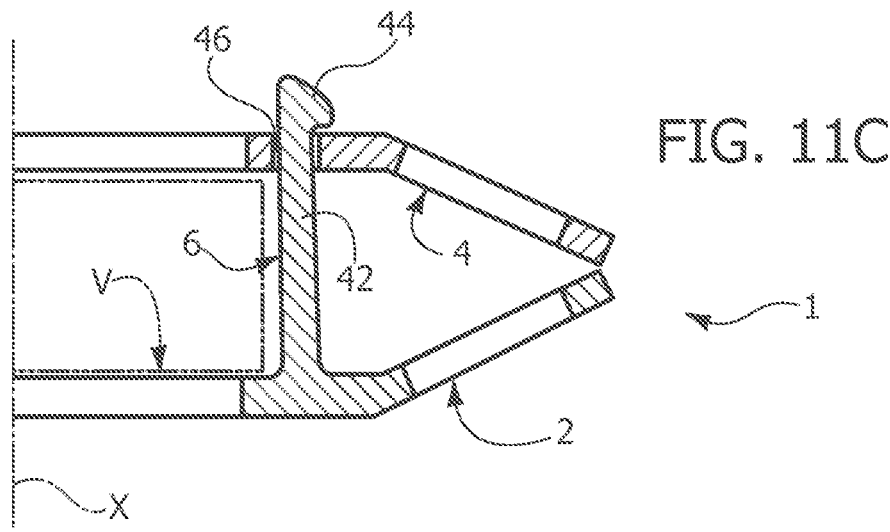

In various embodiments, as exemplified in FIGS. 11A-C, coupling of the anchoring assemblies to the connection structure 6 may be provided in different ways.

In various embodiments, as exemplified in FIG. 11A, the anchoring assembly 2 may be provided integral with the connection structure 6 while the anchoring assembly 4 may be provided as a separate element configured for the engagement within an annular groove G provided in the connection structure 6. In various embodiments, such a mutual arrangement may be reversed, that is with the anchoring assembly 4 integral with the connection structure 6 and the anchoring assembly 2 being a separate element.

In various embodiments, as exemplified in FIG. 11B, the anchoring assembly 2 may be provided integral with the connection structure 6 while the anchoring assembly 4 may be provided as a separate element configured to fit axially on the connection structure 6, supported by an abutment surface 41. The anchoring assembly 4 may then be fixedly attached to the connection structure 6 by means of a ring 42 (e.g., a ring nut or a deformable ring). Again, the mutual arrangement described may be reversed according to the needs.

In various embodiments, as exemplified in FIG. 11C, the anchoring assembly 2 may include a plurality of fingers 42 having a head 44 substantially shaped in a harpoon-like fashion. Each finger 42 may be configured to snap-engage a slot 46, which after the engagement defines an abutment surface for the head 44 which maintains the anchoring assemblies 2, 4 connected to one another. In that case, the connection structure 6 may be provided by a circular array of fingers 42 protruding axially from the anchoring assembly 2.

In various embodiments, such an arrangement may be reversed by providing the fingers 42 on the assembly 4, while in various embodiments the fingers 42 may be provided partly on the assembly 2, and partly on the assembly 4. The prosthesis V may then be housed within a circular "cage" as created by the fingers 42.

Figure 12A:
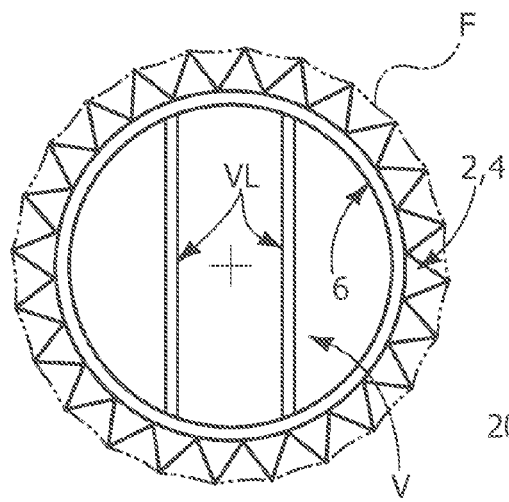
FIGS. 12A-D illustrate embodiments of anchoring devices.
Figure 12B:
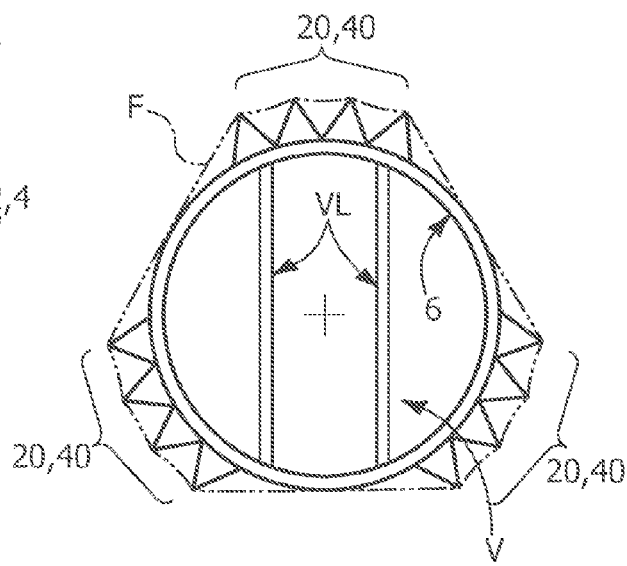

In various embodiments, as exemplified in FIGS. 12A-12B, the anchoring assemblies 2, 4 may be provided as an annular continuum of radially protruding anchoring formations (FIG. 12A), while in other embodiments they may be arranged in separate sectors (defining the anchoring elements 20, 40) of adjacent anchoring formations, as shown in FIG. 12B. In other words, in various embodiments such as those exemplified in FIG. 12A, the device 1 may include a one-by-one alternate arrangement of individual anchoring formations carried by one and the other of the complementary arched portions of the anchoring assemblies 2, 4, respectively. In other embodiments, such as those exemplified in FIG. 12B, instead, the device 1 may include an alternate arrangement of groups of anchoring formations, such alternated groups being carried by one and the other of the complementary arched portions of the anchoring assemblies 2, 4, respectively.

In various embodiments, the anchoring assemblies 2, 4 may include a sealing member forming an impermeable surface coupled to at least one of the anchoring assemblies. In various embodiments, the sealing member may extend to cover the anchoring formations (e.g., the anchoring formations 16, 18, 24, 32) of the corresponding anchoring assembly 2, 4.

In various embodiments, such sealing member may be a sheath, preferable a textile sheath, F (illustrated in phantom line) vested onto at least one of the anchoring assemblies. Such sheath F may provide a sealing action (e.g., against blood leaks) between the anchoring device 1 and the implantation and may be configured to promote tissue covering (regrowth).

In various embodiments, the anchoring assemblies 2, 4 may exhibit a discontinuous structure (as exemplified in FIG. 12B) and the anchoring device 1 may be provided with a continuous fabric enclosure F to prevent blood leaks.

Figure 12C:
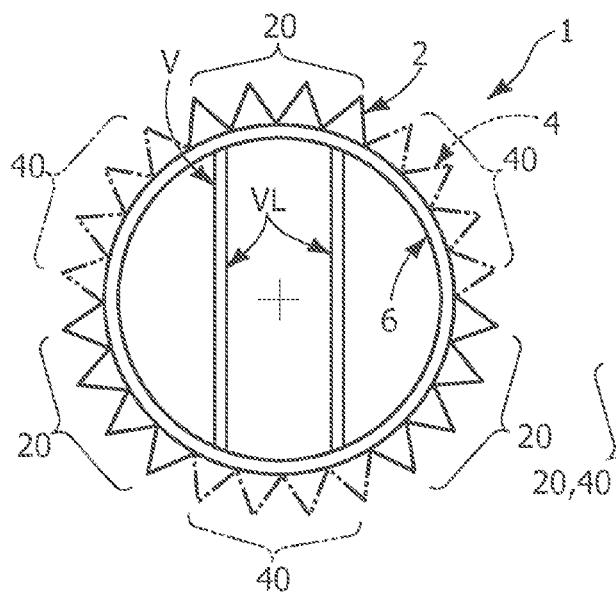
Figure 12D:
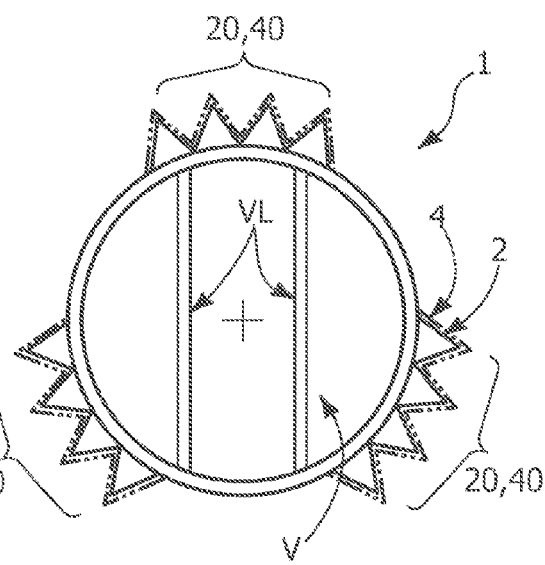

In various embodiments, as exemplified in FIGS. 12C and 12D, sectors 20, 40 of the anchoring assemblies 2, 4 may be arranged in an alternated fashion (FIG. 12C) or substantially overlapped (FIG. 12D).

In various embodiments, a combination of such arrangements may be provided, with the sectors 20, 40 at least partly overlapping.

FIGS. 13 to 19 illustrate, purely by way of non-limiting example, a method for anchoring a cardiac valve prosthesis with a device according to one or more of the embodiments.

While implantation as described herein refers by way of example to the mitral valve, it will be appreciated that the description applies independently of the implantation site. For example, the skilled artisan will recognize that the methods may apply to implanting a prosthetic valve, e.g., at the pulmonary valve annulus or the tricuspid valve annulus. Also, while implantation as described herein refers to an antegrade approach, this is not to be construed as limitative of the scope of the invention.

With reference to FIG. 13, reference number 100 designates an instrument for positioning and securing to an implantation site an anchoring device according to one or more of the embodiments.

The instrument 100 extends along a longitudinal axis H and may include a handle 102 fitted on a shaft 104 having a tubular element 106 slidably mounted thereon. A sleeve 108 may in turn be slidably mounted on the tubular element 106.

In various embodiments, as exemplified herein, the tubular element 106 carries a first gripping assembly including, e.g., four fingers 111. The fingers 111 may be hinged to the tubular element 106 by "living" hinges L (see FIG. 16) which bias the fingers 111 away from the axis H. In addition to protruding axially, the fingers 111 may also protrude radially.

The sleeve 108 may be configured to slide over the living hinges L and maintain the fingers 111 as close as possible to the axis H.

A second gripping assembly 112 may be in turn be carried by the shaft 104. The gripping assembly 112 has a substantially fork-like arrangement including first and second gripping members 114, 116 each having a respective locking foot 118, 120.

For reasons detailed below, one of the two locking members 114, 116 may be displaceable with respect the position illustrated in FIG. 10.

With reference again to the example of FIG. 11, the anchoring device 1 may be installed on the instrument 100 in a partially disassembled configuration.

In any of the embodiments previously described, the second anchoring assembly 4 may be retained on the fingers 111 while the first anchoring assembly 2 may be installed on the connection structure 6, which houses the cardiac valve prosthesis. The gripping members 114, 116 may be engaged within the connection structure 6, which may be prevented from disengagement by means of the locking feet 118, 120.

At the time the anchoring device 1 and the cardiac valve prosthesis V are mounted on the instrument 100, the tubular element 106, the distal sleeve 108 and the first gripping assembly 110 may be maintained in a proximal position, substantially adjacent to the handle 102, so that the second anchoring assembly may be axially separated with respect to the reminder of the anchoring device 1 (FIG. 13).

It will be appreciated that, as used herein, "proximal" and "distal" refer to the structure of the instrument, with the handle 102 taken as the proximal reference.

The instrument 100 (FIG. 14) may then be advanced to the implantation site to bring the elements of the anchoring device 1 carried by the second gripping assembly 112 on that part of the implantation site opposite to the elements carried by the first gripping assembly 110. The two separate portions of the anchoring device 1 carried by the instrument 100 will thus lie astride of the implantation site (e.g., the mitral valve annulus).

With the second gripping assembly 112 positioned to cause the two portions of the anchoring device 1 to be positioned astride of the valve annulus and the first anchoring assembly 2 in contact with the walls of the implantation site, one or more portion of biological tissue at the implantation site may be trapped by the anchoring assembly 2, for example, by the anchoring formations 24, 32.

If the tines or barbs 36, or any of the teeth 38 and the hooks 39, are provided on the anchoring formations, the biological tissue may be fixed on the anchoring formation 2 by penetrating the tissue with the tines or barbs 36 (or the teeth 38/hooks 39).

The tubular element 106 may be then be advanced along the shaft 104 (i.e., toward the distal end of the instrument) in order to couple the second anchoring assembly 4 on the connection structure 6.

Figure 15:
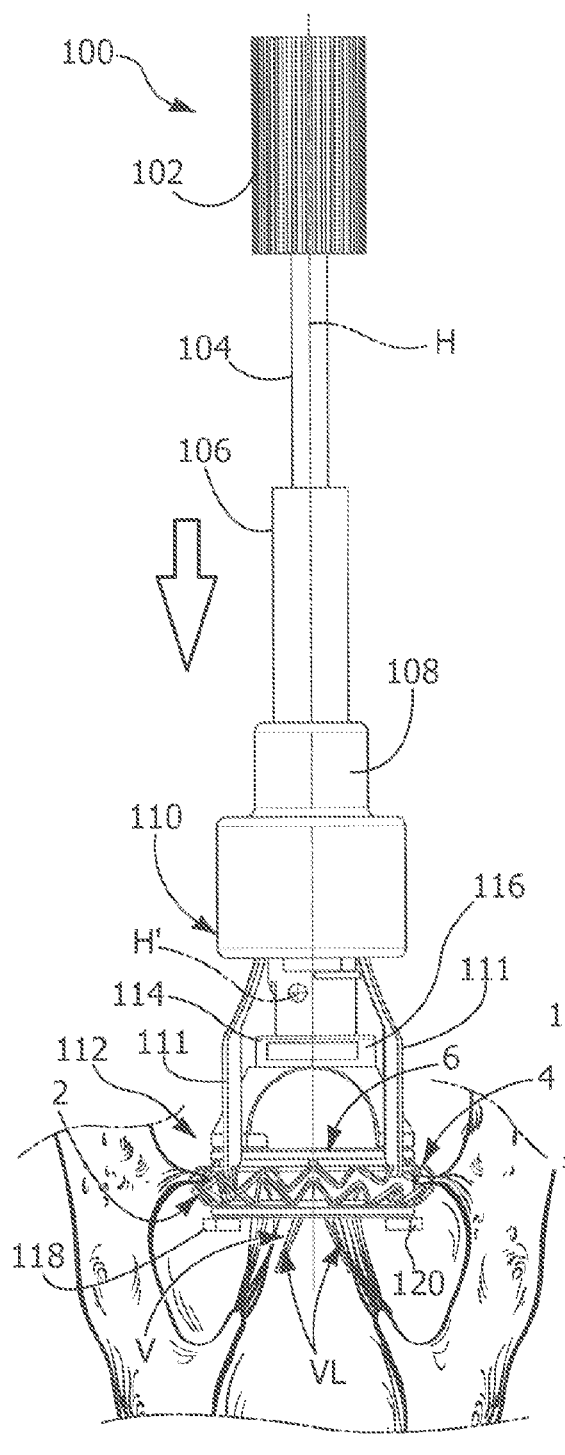

The tissue at the implantation side which was previously trapped on the first anchoring assembly 2 will now be firmly secured (e.g., pinched) by and between the anchoring assemblies 2, 4 coupled by means of the connection structure 6 (FIG. 15).

Figure 16:
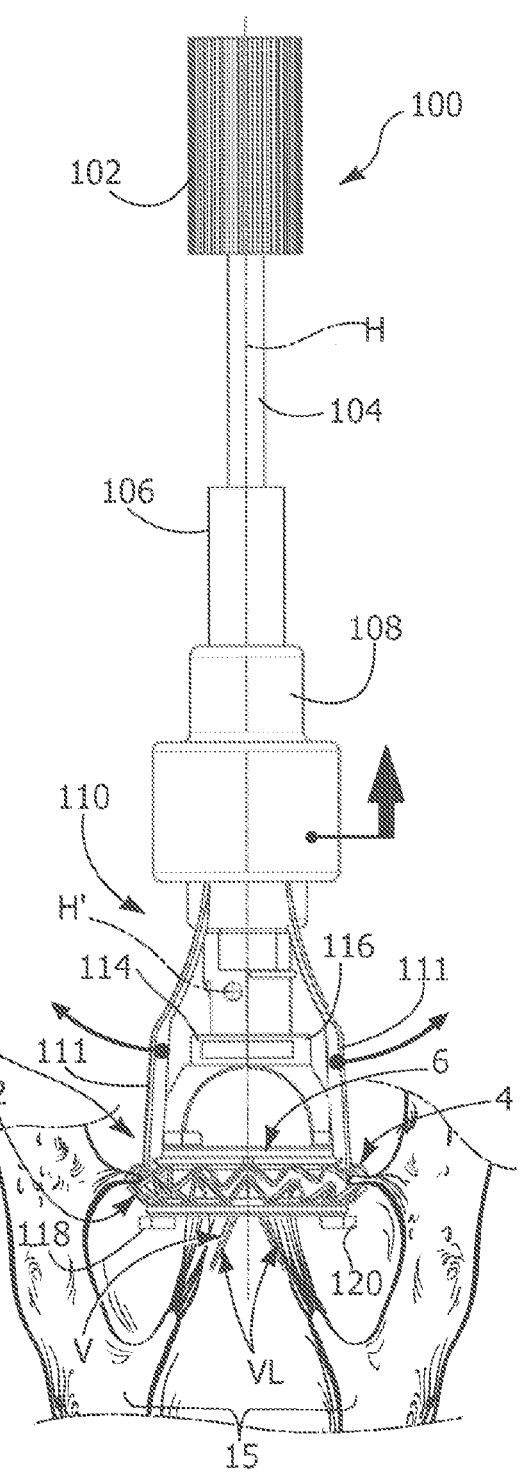
Figure 19:
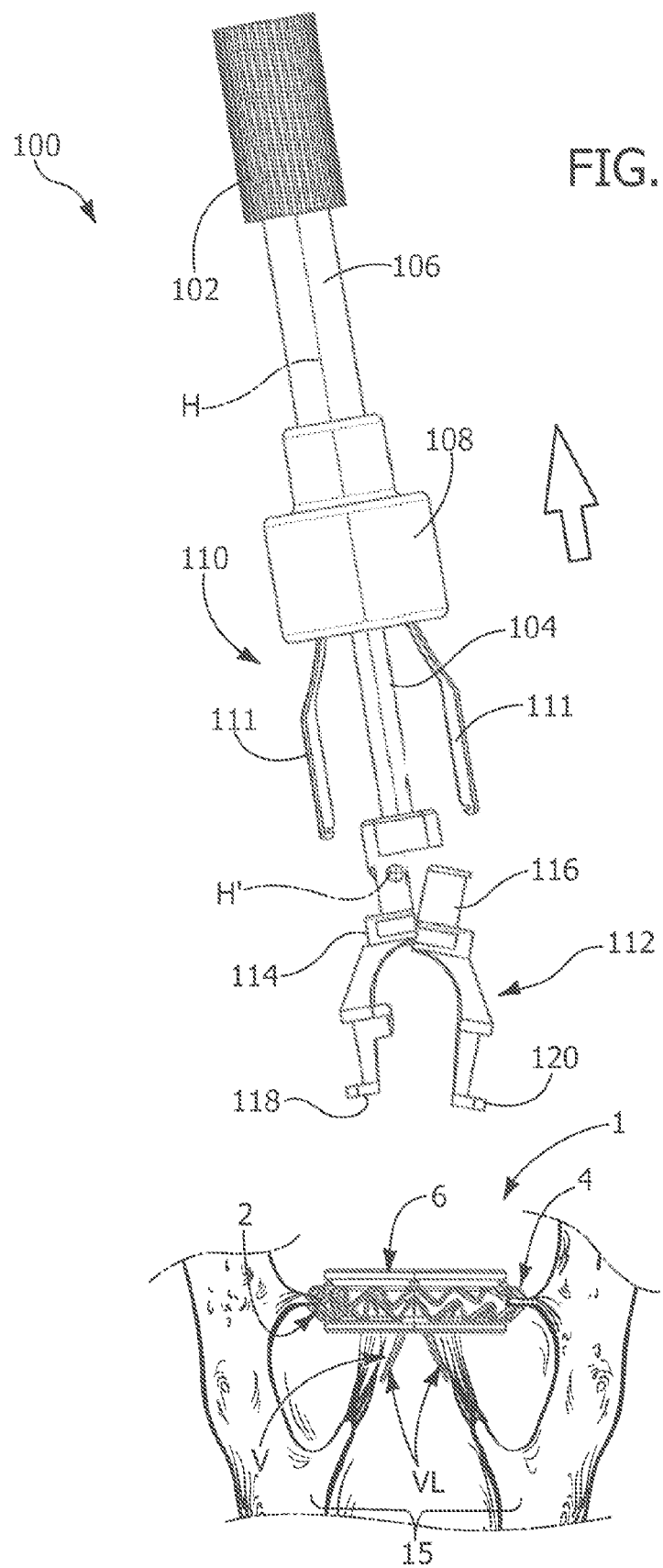

As exemplified in FIG. 16, the sleeve 18 may be then retracted in a proximal direction in order to release the fingers 111 and let them spread apart due to the outward bias of the living hinges L. This will result in the fingers 111 being disengaged from the anchoring assembly 4.

As exemplified in FIG. 17, the tubular element 106 may be retracted in a proximal direction away from the implant site.

In various embodiments, the anchoring assembly 4 may be provided with an open ring structure, and the implantation procedure may be aborted by dilating the anchoring assembly 4 with a dilator tool in a way at least roughly similar to dilating so-called "Seeger" elastic rings in mechanics. The anchoring assembly 4 may be disengaged even if provided as a closed annular element by simply deforming and removing it.

As exemplified in FIG. 18, disengagement of the second gripping assembly 112 from the device 1 and from the cardiac valve prosthesis V may be effected by displacing the gripping element 116 with respect to the gripping member 114. This may be achieved by rotation (here clockwise, see R) around an axis H', transversal the longitudinal axis H, which substantially results in a displacement of the foot 120 inwardly of the connection structure 6, so that the retaining action exerted thereon is released.

The instrument 100 may then be removed by simply withdrawing it from the implantation site as the instrument 100 is no longer coupled to the anchoring device 1.

The cardiac valve prosthesis V may be then fixed to the anchoring device 1, which is in turn firmly anchored to the implantation site due to the pinching action exerted by the anchoring assemblies 2, 4 on the native biological tissue sandwiched (pinched) therebetween.

Accordingly, the anchoring device 1 enables, sutureless implantation of the cardiac valve prosthesis V, which reduces the time required for the intervention (and the complexity thereof as well), to the advantage of the safety for the patient. No time-consuming suturing operations are required by the practitioner, since anchoring at the implantation site is achieved just by manipulating portions of biological tissue at the implantation site in order to trap the tissue between the anchoring formations 2, 4.

In various embodiments, the anchoring assemblies 2, 4 may be a metallic material including chrome-cobalt alloys (Cr—Co alloys), stainless steel, superelastic metal alloys or polymeric materials.

In various embodiments, the stress-strain curve of the material of the anchoring assemblies 2, 4 may be chosen to allow a correct entrapment of the portions of tissue even if the amount or thickness of the biological tissue being trapped may be uneven over the perimeter of the anchoring device. This may be achieved, for example, by using superelastic alloys (e.g., Nitinol).

In various embodiments, the anchoring assemblies 2, 4 may be of an expandable type (e.g., superelastic materials), thus permitting implantation of the device 1 together with the cardiac valve prosthesis V even percutaneously through the vascular system or via small incisions in the skin. In various embodiments, the anchoring assemblies 2, 4 may have a coating which may be biocompatible and hemocompatible.

Naturally, without departing from the principles of the invention, the details and the embodiments may vary, even significantly, with respect to what has been described and illustrated, without departing from the scope of the invention as defined by the annexed claims.

The invention claimed is:

1. A device for anchoring a prosthetic heart valve on biological tissue, the device comprising: first and second anchoring assemblies that are mutually couplable to secure biological tissue therebetween, wherein the anchoring assemblies include at least one pair of complementary arched portions having anchoring formations for anchoring on the biological tissue, such that the anchoring formations include extensions which are rigidly connected to the anchoring assemblies and extend radially outwardly from one of the anchoring assemblies in an aligned arrangement with respect to corresponding extensions extending radially outwardly from the other of the anchoring assemblies, whereby, with the anchoring assemblies mutually coupled to secure the biological tissue therebetween, the extensions in the pair of complementary arched portions form couples of co-operating extensions, wherein, in at least one of the anchoring assemblies, the extensions have different lengths over different portions of the respective anchoring assemblies.

2. The device of claim 1, wherein the extensions are elastically deformable.

3. The device of claim 1, wherein, in at least one of the arched portions, the extensions are bent toward the complementary arched portion.

4. The device of claim 1, wherein, in at least one of the arched portions, the extensions are elastically biased towards the complementary arched portion.

5. The device of claim 1, wherein the extensions taper, preferably sawtooth-like, radially outwardly of the arched portions.

6. The device of claim 1, wherein at least part of the extensions have an apertured structure.

7. The device of claim 1, wherein at least one of the anchoring assemblies includes an annular base body having the anchoring formations as integral extensions thereof.

8. The device of claim 7, wherein the complementary arched portions extend over the whole of the anchoring assemblies, whereby the anchoring formations form a crown of integral extensions surrounding the annular base body.

9. The device of claim 7, wherein the complementary arched portions extend over respective portions of the anchoring assemblies, whereby the anchoring formations include at least one angular sector of integral extensions of the annular base body.

10. A device for anchoring a prosthetic heart valve on biological tissue, the device comprising: First and second anchoring assemblies that are mutually couplable to secure biological tissue therebetween, wherein the anchoring assemblies include: at least one first pair of complementary arched portions having extensions in an aligned arrangement to form couples of co-operating extensions securing therebetween the biological tissue in a linear trajectory; and at least one second pair of complementary arched portions having integral extensions extending radially outwardly of one of the anchoring assemblies in an alternate arrangement with respect to homologous extensions extending radially outwardly of the other of the anchoring assemblies, whereby, with the anchoring assemblies mutually coupled to secure the biological tissue the extensions in the second pair of complementary arched portions interdigitate and impart to the biological tissue secure therebetween a serpentine-like trajectory.

11. The device of claim 10, wherein the anchoring assemblies have a substantially D-shaped plan outline.

12. The device of claim 10, wherein the anchoring assemblies have a substantially D-shaped plan outline, at least one of the first pair of complementary arched portions is arranged at the curved portion of the D-shaped outline, and at least one the second pair of complementary arched portions is arranged at the linear portion of the D-shaped outline.

13. The device of claim 11, wherein at least one the first pair of complementary arched portions is arranged at the curved portions of the D-shaped outline, and at least one of the second pair of complementary arched portions is arranged at the linear portion of the D-shaped outline.

14. The device of claim 3, further comprising a sealing member forming an impermeable surface coupled to at least one of the anchoring assemblies.

15. The device of claim 13, wherein the sealing member is a sheath, preferably a textile sheath, coupled to at least one of the anchoring assemblies.

16. The device of claim 13, wherein the sealing member extends to cover the extensions.

\* \* \* \* \*